US011560358B2

(12) United States Patent
Pop et al.

(10) Patent No.: US 11,560,358 B2
(45) Date of Patent: Jan. 24, 2023

(54) RESVERATROL-PIPERAZINE CO-CRYSTALS

(71) Applicant: LETAVIS AB, Alta (SE)

(72) Inventors: Mihaela Maria Pop, Amsterdam (NL); Paula Vasilichia Bulieris, Cluj-Napoca (RO); Ingemar Pongratz, Alta (SE); Victor Fruth-Oprisan, Bucharest (RO); Raul-Augustin Mitran, Bucharest (RO)

(73) Assignee: LETAVIS AB, Älta (SE)

( * ) Notice: Subject to any disclaimer, the term of this patent is extended or adjusted under 35 U.S.C. 154(b) by 0 days.

(21) Appl. No.: 17/046,120

(22) PCT Filed: Apr. 9, 2019

(86) PCT No.: PCT/EP2019/058878
§ 371 (c)(1),
(2) Date: Oct. 8, 2020

(87) PCT Pub. No.: WO2019/197366
PCT Pub. Date: Oct. 17, 2019

(65) Prior Publication Data
US 2021/0032210 A1 Feb. 4, 2021

(30) Foreign Application Priority Data
Apr. 11, 2018 (SE) .................... 1850403-5

(51) Int. Cl.
*C07D 241/04* (2006.01)
*C07C 29/78* (2006.01)
*C07C 49/255* (2006.01)

(52) U.S. Cl.
CPC ............ *C07D 241/04* (2013.01); *C07C 29/78* (2013.01); *C07C 49/255* (2013.01); *C07B 2200/13* (2013.01)

(58) Field of Classification Search
CPC ....... C07C 29/78; C07C 39/21; C07C 49/225; C07C 49/255; C07B 2200/13
See application file for complete search history.

(56) References Cited

FOREIGN PATENT DOCUMENTS

| WO | 2005/000780 | 1/2005 |
|----|-------------|--------|
| WO | 2015/052568 | 4/2015 |

OTHER PUBLICATIONS

Mehta, Basant Kumar et al., Crystal Growth & Design (2018) vol. 18, p. 1581-1592 and supporting information.*
The International Search Report (ISR) with Written Opinion for PCT/EP2019/058878 dated Jun. 25, 2019, pp. 1-17.
The International Preliminary Report on Patentability (IPRP) for PPCT/EP2019/058878 dated May 12, 2020, pp. 1-9.
Mehta, Basant Kumar et al. "Rational Coformer Selection and the Development of New Crystalline Multi component Forms of Resveratrol with Enhanced Water Solubility" Crystal Growth & Design (2018) vol. 18(3), pp. 1581-1592.
Mehta, Basant Kumar et al. "Supporting Information File Rational Coformer Selection and the Development of New Crystalline Multicomponent Forms of Resveratrol with Enhanced" Crystal Growth & Design (2018) vol. 18(3), pp. S1-S19. XP055594039. Retrieved from the Internet: URL:https://pubs.acs.org/doi/abs/10.1021/acs.cgd.7b01537#notes-1 [retrieved on Jun. 4, 2019].
Caira, Mino R. "Crystalline Polymorphism of Organic Compounds" Topics in Current Chemistry (1998) vol. 198, pp. 164-208.
He, Hongyan et al. "Modulating the Dissolution and Mechanical Properties of Resveratrol by Cocrystallization" Crystal Growth & Design (2017) vol. 17(7), pp. 3989-3996.
Zhengzheng, Zhou et al. "Resveratrol cocrystals with enhanced solubility and tabletability" International Journal of Pharmaceutics (2016) vol. 509(1), pp. 391-399.

* cited by examiner

*Primary Examiner* — Valerie Rodriguez-Garcia
(74) *Attorney, Agent, or Firm* — Ballard Spahr LLP

(57) ABSTRACT

The present document is directed to co-crystals of resveratrol and/or curcumin with piperazine and their use in medicine and/or as food and feed supplements.

14 Claims, 17 Drawing Sheets a)

b)

Resveratrol

Piperazine

Keto form of curcumin

Enol form of curcumin

RESVERATROL-PIPERAZINE CO-CRYSTALS

CROSS REFERENCE TO RELATED APPLICATION

This application is a U.S. national phase of International Application No. PCT/EP2019/058878, filed Apr. 9, 2019, which claims priority to Swedish Patent Application No. 1850403-5, filed Apr. 11, 2018, both of which are incorporated by reference herein in their entirety.

TECHNICAL FIELD

The present document is directed to co-crystalline forms of substances that can be used as food or feed supplements or medical substances for improving animal health.

BACKGROUND

Animal health and welfare is not only an ethical aspect, but is a key financial issue in animal production and to secure the food supply. Poor animal husbandry conditions promote diseases, associated with losses in productivity. At the same time, food production typically requires large scale production facilities which in general represent disease promoting conditions. Ethical and economic reasons thus push a constant search for alternative products to promote health and reduce disease susceptibility. Meat production from swine is a major societal sector and food source for human feed and represents a major market.

Ileitis (also known as porcine enteropathy, porcine proliferative enteropathy, and porcine proliferative enteritis) is a serious problem in the breeding of swine where it is estimated that 50-70% of all the pigs are afflicted which causes major economic losses for the breeders and suffering for the animals.

Ileitis is an inflammation of the ileum in the lower part of the small intestine, affecting both humans and farmed animals. Ileitis causes the immune system to attack cells in the intestine, thus leading to a decreased nutritional uptake. Symptoms include chronic or intermittent diarrhea, abdominal cramps, fever, weakness, weight loss, and anemia may also occur. In swine farming, ileitis causes piglets to lose weight, due to the transition to solid food and un-developed gastrointestinal environment and function, with considerable losses to the producers. The microbial flora of the intestine is also affected which leads to an increased sensitivity to other microbial infections.

In order to treat ileitis the breeders administer large amounts of antibiotics to the animals, which e.g. increases the risk for antibiotic resistance development.

As an alternative to using antibiotics, animal producers have administered plant extracts or ZnO via the feed but these strategies have either been inefficient (plant extracts) or are associated with health risks (ZnO).

Compounds such as curcumin and resveratrol are diet derived compounds with well documented health promoting effects. Interestingly, both curcumin and resveratrol have been shown to be efficient alternatives to reduce the symptoms associated with certain autoimmune diseases such as rheumatoid arthritis and IBD in a number of animal models, including swine. The biological mechanism of action of these compounds is presumed to be coupled to their ability to reduce the activity of a subset of immune cells, TH17 cells, and/or to increase the activity of T-reg immune cells and through this mechanism reduce the immunological response that leads to autoimmune diseases including IBD and Ileitis.

Curcumin is a curcuminoid from turmeric with proven beneficial effects after consumption. These effects include anti-inflammatory, antioxidant and anti-cancer effects. Curcumin has also been shown to have beneficial effects on the heart and to support and protect cognitive processes in the brain. Further it can improve insulin secretion and insulin sensitivity. Curcumin has been suggested for use in the treatment/prevention of osteoarthritis, prostate cancer, colon cancer, skin cancer, breast cancer, arteriosclerosis, digestive problems, ulcerative colitis, dementia and metabolic syndrome. However, the oral bioavailability of curcumin is low and it is also a fat-soluble substance, which must be taken into account when formulating curcumin.

Resveratrol may be found in red grapes, Japanese knotweed (*Polygonum cuspidatum*, a common source for industrial purposes), grapes, tomatoes, raspberries, plums, and peanuts. Resveratrol has antioxidant, anti-inflammatory, and anti-cancer effects and can also protect the heart and brain. It is the trans-form of the molecule that has mainly been studied in terms of physiological effects. The cis-form has similar anti-oxidant properties but fail to mimic the anti-inflammatory and anti-cancer effects of the trans-form. Resveratrol has been suggested for use in protection against cancer in skin, prostate, colon, lung, breast, liver, protection against heart disease and arteriosclerosis, for lowering the blood pressure and improving insulin-sensitivity in type II diabetes, in metabolic syndrome and Alzheimer's disease, as having positive effects on mental disorders, ulcerative colitis, in different gastrointestinal porcine diseases such as ileitis, porcine enteropathy, proliferative haemorrhagic enteropathy and as an anti-inflammatory agent. Resveratrol is generally well tolerated after administration but has a low bioavailability due to low solubility in body fluids. Resveratrol is conjugated via sulphation and glucuronidation (P450 enzymes) that reduce the amount of free resveratrol.

Although therapeutic or clinical efficacy is the primary concern for a drug (or an active nutraceutical ingredient), the solid-state form (i.e., the crystalline or amorphous form) of a drug candidate can be critical to its pharmacological properties and to its development as a viable drug. Crystalline forms of drugs have been used to alter the physicochemical properties of a particular drug. Each crystalline form of a drug candidate can have different solid-state (physical and chemical) properties, which may be relevant for drug delivery. Crystalline forms often have better chemical and physical properties than corresponding non-crystalline forms, such as the amorphous form. The differences in physical properties exhibited by a novel solid form of a drug (such as a co-crystal or polymorph of the original drug) affect pharmaceutical parameters such as storage stability, compressibility and density (relevant for formulation and product manufacturing), and dissolution rates and solubility (relevant factors in achieving suitable bioavailability).

Co-crystals of nutraceutical compounds, including curcumin and resveratrol have been disclosed previously in e.g. WO2008153945A2, WO2015052568A2, U.S. Pat. No. 8,399,712B2, Cryst. Growth Des. 2011, 11, 4135-4145, International Journal of Pharmaceutics 509 (2016) 391-399. Although one may envisage a large amount of combinations with possible co-formers not all the combinations will lead to co-crystals, or stable solid forms. Further, although there is a good understanding of the co-crystal components in terms of their physical and chemical properties, elucidation of their a priori interaction in a new co-crystal structure is not possible, as the interactions that determine the structure are relatively weak and the number of degrees of freedom for the optimization problem is immeasurable.

SUMMARY

One aim of the present document is to refine and/or improve substances naturally present in food and/or feed stuff in order to increase their usefulness as regards e.g. production, storage stability and/or bioavailability.

The present document thus provides a resveratrol-piperazine co-crystal, Form 1, characterized by having an XRPD pattern comprising peaks at 4.48, 13.32, 16.96, 18.88, 19.16, and 22.84 °2θ±0.2 °2θ, an XRPD pattern according to Table 1, an XRPD pattern as shown in FIG. 1, by having a fusion temperature $T_{fus}$ of 201° C.±5° C., and/or by having a DSC thermogram as shown in FIG. 2.

The present document also provides a method for producing the resveratrol-piperazine co-crystal, Form 1, as defined herein, said method comprising the steps of:
 a) dispensing resveratrol in acetone or acetonitrile;
 b) adding piperazine in acetone or acetonitrile to the dispensed resveratrol of step a) thereby providing a resveratrol-piperazine mixture;
 c) optionally diluting the resveratrol-piperazine mixture obtained in step b) with acetone or acetonitrile;
 d) heating the resveratrol-piperazine mixture obtained in step b) or c) at a temperature within the range of from about 30° C. to about 50° C. under stirring for about 10-30 minutes thereby providing a resveratrol-piperazine suspension;
 e) allowing the resveratrol-piperazine suspension obtained in step d) to settle;
 f) separating a solid phase obtained in step e); and
 g) drying the separated solid phase of step f).

The present document also discloses a method for producing the resveratrol-piperazine co-crystal, Form 1, as defined herein, said method comprising the steps of:
 a) dispensing resveratrol in ethanol;
 b) adding piperazine in ethanol to the dispensed resveratrol of step a) thereby providing a resveratrol-piperazine mixture;
 c) diluting the resveratrol-piperazine mixture obtained in step b) with ethanol;
 d) placing a vessel containing the mixture of step c) within a further vessel containing a solvent such as tert-butyl methyl ether, wherein the mixture of the vessel and the solvent of the further vessel are kept separate from each other;
 e) closing the further vessel;
 f) allowing the further vessel of step e) to stand for about 7 to about 14 days, such as about 10 days,
 g) optionally removing the vessel from the further vessel, and
 h) allowing any solvent remaining in the vessel of step f) or step g) to evaporate.

The present document also discloses a method for producing the resveratrol-piperazine co-crystal, Form 1, as defined herein, said method comprising the steps of:
 a) subjecting a mixture comprising resveratrol, piperazine and a solvent such as ethanol to grinding such as grinding in a ball mill;
 b) allowing the mixture of step a) to dry thereby providing a further mixture; and
 c) optionally subjecting the further mixture to further grinding.

The present document also discloses a method for producing the resveratrol-piperazine co-crystal, Form 1, as defined herein, said method comprising the steps of:
 a) adding equimolar amounts of resveratrol and piperazine to a heating device, such as an aluminum pan or hot melt extrusion equipment;
 b) heating said resveratrol and said piperazine, such as at a temperature of 100° C. or more, until the resveratrol and piperazine have melted and formed a melted mixture;
 c) allowing said melted mixture to cool down.

The present document also provides a resveratrol-piperazine co-crystal, Form 1, obtained or obtainable by any of the methods disclosed herein.

The present document also provides a resveratrol-piperazine co-crystal, Form 2, characterized by having an XRPD pattern comprising peaks at 5.87, 12.74, 17.43, 17.70, 20.55, and 21.32 °2θ±0.2 °2θ, an XRPD pattern according to Table 2, an XRPD pattern as shown in FIG. 3, by having a fusion temperature $T_{fus}$ of 199° C.±5° C., and/or by having a DSC thermogram as shown in FIG. 4.

The present document also provides a method for producing the resveratrol-piperazine co-crystal, Form 2, as defined herein, said method comprising the steps of:
 a) mixing resveratrol with a solution of piperazine such as a tetrahydrofurane solution of piperazine;
 b) adding a further solvent such as tetrahydrofurane to the mixture obtained in step a);
 c) placing a vessel containing the solution of step b) within a further vessel containing a solvent such as tert-butyl methyl ether, wherein the solution of the vessel and the solvent of the further vessel are kept separate from each other;
 d) closing the further vessel;
 e) allowing the further vessel of step d) to stand for about 7 to about 14 days, such as about 10 days;
 f) optionally removing the vessel from the further vessel; and
 g) allowing any solvent remaining in the vessel of step e) or step f) to evaporate.

The present document also provides a method for producing the resveratrol-piperazine co-crystal, Form 2, as defined herein, said method comprising the steps of:
 a) subjecting a mixture comprising resveratrol, piperazine and a solvent such as tetrahydrofuran to grinding such as grinding in a ball mill;
 b) allowing the mixture of step a) to dry thereby providing a further mixture; and
 c) optionally subjecting the further mixture of step b) to further grinding.

The present document also provides a resveratrol-piperazine co-crystal, Form 2, obtained or obtainable by the any of the methods disclosed herein.

The present document also provides a curcumin-piperazine co-crystal, Form 1, characterized by having an XRPD pattern comprising peaks at 4.60, 9.18, 11.31, 13.12, 14.73, 16.97, 22.98, and 24.66 2θ, an XRPD pattern according to Table 3, an XRPD pattern as shown in FIG. 5, by having a fusion temperature $T_{fus}$ of 94° C.±5° C., and/or by having a DSC thermogram as shown in FIG. 6.

The present document also provides a method for producing the curcumin-piperazine co-crystal, Form 1, as defined herein, said method comprising the steps of:
 a) mixing:
  (i) a solution of curcumin, such as an acetonitrile solution of curcumin, and (ii) a solution of piperazine, such as an acetonitrile solution of piperazine;
b) stirring the mixture obtained in step a) at a temperature within the range of from about 40° C. to about 80° C., such as about 60° C., for a time of about 1 minute to about 60 minutes, such as 5 minutes;
c) allowing the mixture obtained in step b) to settle thereby providing a solid phase and a liquid phase;
d) separating the solid phase from the liquid phase; and
e) drying the solid phase.

The present document also provides a curcumin-piperazine co-crystal, Form 1, obtained or obtainable by the method disclosed herein.

The present document also provides a curcumin-piperazine co-crystal, Form 2, characterized by having an XRPD pattern comprising peaks at 4.93, 9.46, 9.85, 13.98, 17.77, and 21.48 °2θ±0.2 °2θ, an XRPD pattern according to Table 4, an XRPD pattern as shown in FIG. 7, by having a fusion temperature $T_{fus}$ of 87° C.±5° C., and/or by having a DSC thermogram as shown in FIG. 8.

The present document also provides a method for producing the curcumin-piperazine co-crystal, Form 2, as defined in herein, said method comprising the steps of
a) mixing:
  (i) a solution of curcumin, such as a tetrahydrofurane solution of curcumin, and
  (ii) a solution of piperazine, such as a tetrahydrofurane;
b) placing a vessel containing the mixture obtained in step a) within a further vessel containing a solvent such as hexane, wherein the mixture of the vessel and the solvent of said further vessel are kept separate from each other;
c) closing the further vessel;
d) allowing the further vessel of step c) to stand for about 7 to about 14 days such as 10 days;
e) optionally removing the vessel from the further vessel; and
f) allowing any solvent remaining in the vessel of step d) or step e) to evaporate.

The present document also provides a method for producing the curcumin-piperazine co-crystal, Form 2, as defined herein, said method comprising the steps of:
a) subjecting a mixture of curcumin, piperazine and a solvent, such as tetrahydrofuran, to grinding such as grinding in a ball mill;
b) allowing the mixture of step a) to dry thereby providing a further mixture; and
c) optionally subjecting the further mixture of step b) to further grinding.

The present document also provides a curcumin-piperazine co-crystal, Form 2, obtained or obtainable by any of the methods disclosed herein.

The present document also provides a resveratrol-piperazine-curcumin co-crystal characterized by having an XRPD pattern comprising peaks at 4.26, 11.86, 16.78, 23.46, and 25.68 °2θ±0.2 °2θ, an XRPD pattern according to Table 5, an XRPD pattern as shown in FIG. 9, by having a fusion temperature $T_{fus}$ of 105° C.±5° C. and/or a DSC thermogram as shown in FIG. 10.

The present document also provides a method for producing the resveratrol-piperazine-curcumin co-crystal, as defined herein, said method comprising the steps of:
a) mixing:
  (i) a solution of curcumin, such as an acetone solution of curcumin, and
  (ii) a solution of resveratrol, such as an acetone solution of resveratrol, optionally under stirring;
b) adding a solution of piperazine, such as an acetone solution of piperazine, to the mixture obtained in step a), optionally under stirring;
c) placing a vessel containing the mixture obtained in step b) within a further vessel containing a solvent such as hexane, wherein the mixture of the vessel and the solvent of the further vessel are kept separate from each other;
d) closing the further vessel;
e) allowing the further vessel of step d) for about 7 to about 14 days, such as about 10 days;
f) optionally removing the vessel from the further vessel; and
g) allowing any solvent remaining in the vessel of step e) or step f) to evaporate.

The present document also discloses a resveratrol-piperazine-curcumin co-crystal, obtained or obtainable by a method disclosed herein.

The present document also provides a composition, such as a health supplement, food or feed composition, or a food or feed additive, comprising one or more of a co-crystal as defined herein.

The present document is also directed to co-crystal as defined herein for use as a medicament.

The present document is also directed to a resveratrol-piperazine co-crystal and/or a resveratrol-piperazine-curcumin co-crystal as defined herein for use in the treatment and/or prevention of skin cancer, prostate cancer, colon cancer, lung cancer, breast cancer, liver cancer, heart disease, arteriosclerosis, hypertension, type II diabetes, metabolic syndrome, Alzheimer's disease, Crohn's Disease, Inflammatory Bowel Disease, autoimmune inflammatory diseases, mental disorder, ulcerative colitis, ileitis, porcine enteropathy, proliferative haemorrhagic enteropathy, and/or inflammation.

The present document is also directed to the use of a resveratrol-piperazine co-crystal and/or a resveratrol-piperazine-curcumin co-crystal as defined herein for the preparation of a medicament for the treatment and/or prevention of skin cancer, prostate cancer, colon cancer, lung cancer, breast cancer, liver cancer, heart disease, arteriosclerosis, hypertension, type II diabetes, metabolic syndrome, Alzheimer's disease, Crohn's Disease, Inflammatory Bowel Disease, autoimmune inflammatory diseases, mental disorder, ulcerative colitis, ileitis, porcine enteropathy, proliferative haemorrhagic enteropathy, and/or inflammation.

Further disclosed herein is a method for treating and/or preventing skin cancer, prostate cancer, colon cancer, lung cancer, breast cancer, liver cancer, heart disease, arteriosclerosis, hypertension, type II diabetes, metabolic syndrome, Alzheimer's disease, Crohn's Disease, Inflammatory Bowel Disease, autoimmune inflammatory diseases, mental disorder, ulcerative colitis, ileitis, porcine enteropathy, proliferative haemorrhagic enteropathy, and/or inflammation comprising administering a pharmaceutically acceptable amount of a resveratrol-piperazine co-crystal and/or a resveratrol-piperazine-curcumin co-crystal as defined herein to a subject in need thereof.

The present document also discloses a curcumin-piperazine co-crystal and/or a resveratrol-piperazine-curcumin co-crystal as defined herein for use in the treatment and/or prevention of osteoarthritis, prostate cancer, colon cancer, skin cancer, breast cancer, arteriosclerosis, digestive problems, ulcerative colitis, Crohn's Disease, Inflammatory Bowel Disease, autoimmune inflammatory diseases, dementia and/or metabolic syndrome.

Further disclosed herein is the use of a curcumin-piperazine co-crystal and/or a resveratrol-piperazine-curcumin co-crystal as defined herein for the preparation of a medicament for the treatment and/or prevention of osteoarthritis, prostate cancer, colon cancer, skin cancer, breast cancer, arteriosclerosis, digestive problems, ulcerative colitis, Crohn's Disease, Inflammatory Bowel Disease, autoimmune inflammatory diseases, dementia and/or metabolic syndrome.

The present document is also directed to a method for treating and/or preventing osteoarthritis, prostate cancer, colon cancer, skin cancer, breast cancer, arteriosclerosis, digestive problems, ulcerative colitis, Crohn's Disease, Inflammatory Bowel Disease, autoimmune inflammatory diseases, dementia and/or metabolic syndrome comprising administering a pharmaceutically acceptable amount of a curcumin-piperazine co-crystal and/or a resveratrol-piperazine-curcumin co-crystal as defined herein to a subject in need thereof.

The present document also discloses a resveratrol-piperazine-curcumin co-crystal as defined herein for use in the treatment and/or prevention of skin cancer, prostate cancer, colon cancer, lung cancer, breast cancer, liver cancer, heart disease, arteriosclerosis, hypertension, type II diabetes, metabolic syndrome, Alzheimer's disease, Crohn's Disease, Inflammatory Bowel Disease, autoimmune inflammatory diseases, mental disorder, ulcerative colitis, ileitis, porcine enteropathy, proliferative haemorrhagic enteropathy, inflammation, osteoarthritis, arteriosclerosis, digestive problems, dementia and/or metabolic syndrome.

The present document also discloses the use of a resveratrol-piperazine-curcumin co-crystal as defined herein for the preparation of a medicament for the treatment and/or prevention of skin cancer, prostate cancer, colon cancer, lung cancer, breast cancer, liver cancer, heart disease, arteriosclerosis, hypertension, type II diabetes, metabolic syndrome, Alzheimer's disease, Crohn's Disease, Inflammatory Bowel Disease, autoimmune inflammatory diseases, mental disorder, ulcerative colitis, ileitis, porcine enteropathy, proliferative haemorrhagic enteropathy, inflammation, osteoarthritis, arteriosclerosis, digestive problems, dementia and/or metabolic syndrome.

The present document also discloses a method for treating and/or preventing skin cancer, prostate cancer, colon cancer, lung cancer, breast cancer, liver cancer, heart disease, arteriosclerosis, hypertension, type II diabetes, metabolic syndrome, Alzheimer's disease, Crohn's Disease, Inflammatory Bowel Disease, autoimmune inflammatory diseases, mental disorder, ulcerative colitis, ileitis, porcine enteropathy, proliferative haemorrhagic enteropathy, inflammation, osteoarthritis, arteriosclerosis, digestive problems, dementia and/or metabolic syndrome comprising administering a pharmaceutically acceptable amount of a resveratrol-piperazine-curcumin co-crystal as defined herein, to a subject in need thereof.

The present document also provides the use of a resveratrol-piperazine, curcumin-piperazine and/or a resveratrol-piperazine-curcumin co-crystal as defined herein as a health supplement, food or feed composition, or a food or feed additive.

Further, the present document discloses the use of a resveratrol-piperazine, curcumin-piperazine and/or a resveratrol-piperazine-curcumin co-crystal as defined herein for increasing the growth of live-stock, such as swine.

The present document also discloses a resveratrol-piperazine, curcumin-piperazine and/or a resveratrol-piperazine-curcumin co-crystal as defined in herein for use in the treatment and/or prevention of ileitis and/or a bacterial infection, such as in live-stock, such as swine and/or poultry The present document is also directed to the use of a resveratrol-piperazine, curcumin-piperazine and/or a resveratrol-piperazine-curcumin co-crystal as defined herein for the preparation of a medicament for the treatment and/or prevention of ileitis and/or a bacterial infection in a subject in need thereof, such as in live-stock, such as swine and/or poultry.

Further the present document discloses a method for treating and/or preventing ileitis and/or a bacterial infection, such as in live-stock, such as swine and/or poultry comprising administering a pharmaceutically acceptable amount of a resveratrol-piperazine, curcumin-piperazine and/or a resveratrol-piperazine-curcumin co-crystal as defined herein to a subject in need thereof.

Further, the present document discloses the use of a resveratrol-piperazine, curcumin-piperazine and/or a resveratrol-piperazine-curcumin co-crystal as defined herein for stabilizing a microbial flora, such as a gut microbial flora.

Other features and advantages of the invention will be apparent from the following detailed description, drawings, examples, and from the claims.

Definitions

In the present document the term "co-crystal" is understood as a solid that is a crystalline single phase material composed of two or more different molecular and/or ionic compounds, generally in a stoichiometric ratio, which are neither solvates nor simple salts.

DETAILED DESCRIPTION

Figure 1:
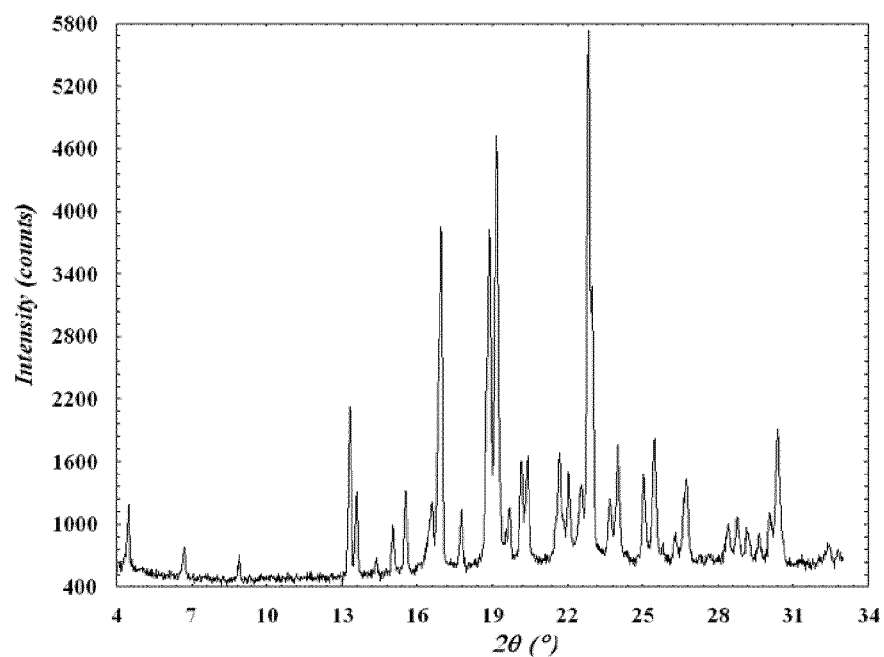
FIG. 1. a) X-ray powder diffraction pattern of the resveratrol-piperazine co-crystal, Form 1, b) shows an overlay of the XRPD pattern for the resveratrol-piperazine co-crystal, Form 1, with the resveratrol-piperazine co-crystal, Form 1, prepared in the upscaled grinding method.
Figure 1:
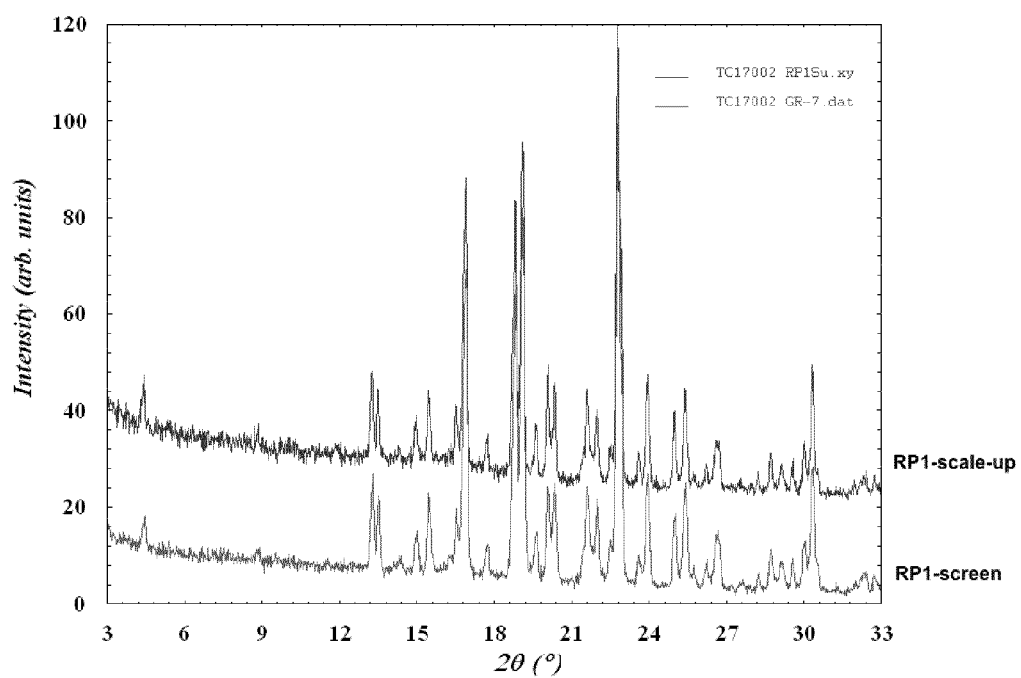

Plants may contain substances with beneficial effects on health. The natural amount of such substances is however often too low to cause these beneficial effects if the plant as such is used as a food or feed. Even if it in some instances is possible to isolate the beneficial substance from its source, such purified substances often have problems with low solubility and/or low stability upon storage.

One aim of the present document is to prepare new forms of curcumin and resveratrol that have properties making them useful as food and feed supplements.

The present inventors have identified piperazine as a bridge/crystal stabilizer and were thereby able to obtain stable co-crystal forms of curcumin and resveratrol with piperazine, which co-crystals are suitable for use as e.g. food or feed additives. Piperazine is in itself a beneficial compound with anti-helminthic properties that also display benefits for gastrointestinal health of animals.

The co-crystals produced are pure compounds with high solubility in water. Low solubility severely impairs the biological availability of the parent curcumin and resveratrol compounds for medicinal/health promoting purposes. Most of the curcumin and resveratrol products available on the market today display very low water-solubility, dramatically reducing the dose vs. effect efficacy of the products when administered through oral routes. The co-crystals disclosed herein bypass this major limitation in solubility while at the same time delivering the pure compound without a need for solubility-increasing agents such as liposomal coating, micronized power and other additives that may carry undesirable side effects.

Finding the right conditions to obtain a co-crystallisation between two or more molecules is not a trivial task as there is a high probability that the component molecules will crystallize by themselves, instead of co-crystallizing together into a co-crystal. Despite this well-known problem of finding the appropriate conditions for co-crystallization, the present inventors were unexpectedly able to prepare stable co-crystals of curcumin and resveratrol with piperazine. When producing the co-crystals disclosed herein, curcumin or resveratrol are typically added in a molar ratio of 1:1 to piperazine. For the production of a resveratrol-piperazine-curcumin co-crystal disclosed herein a molar ratio of 1:1:1 of resveratrol-piperazine-curcumin may be used. The crystals produced were shown to have a 1:1 ratio of curcumin or resveratrol to piperazine.

Co-Crystals and Methods for their Production

In all methods for producing the co-crystals disclosed herein, the compounds used for forming the co-crystal are added in a molar ratio of about 1:1, i.e. for the resveratrol-piperazine and curcumin-piperazine co-crystals, the resveratrol and curcumin, respectively are mixed in a molar ratio of 1:1 to the piperazine. For the resveratrol-piperazine-curcumin co-crystal, resveratrol, piperazine and curcumin are mixed in a molar ratio of 1:1:1.

Figure 2:
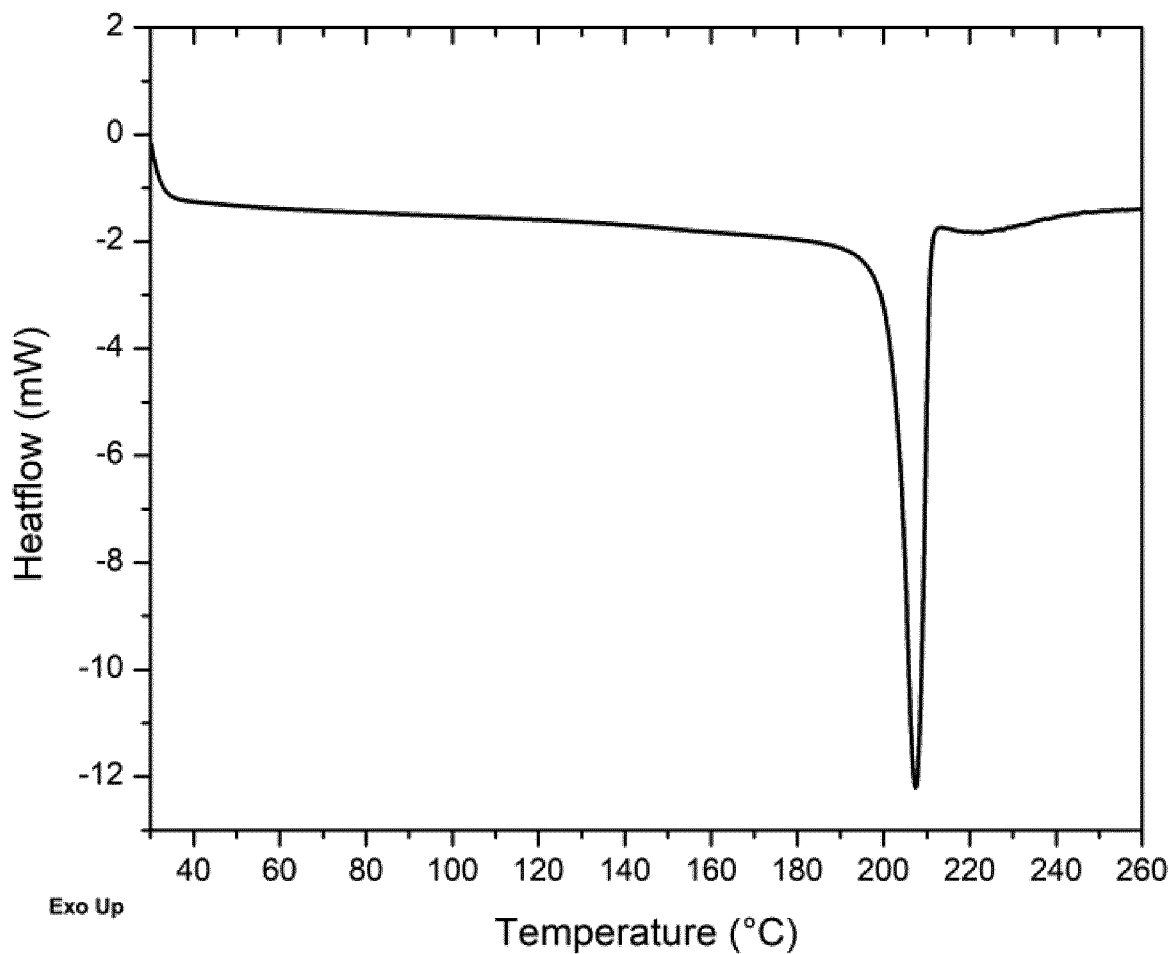
FIG. 2. DSC thermogram of the resveratrol-piperazine co-crystal, Form 1.

The present document discloses a resveratrol-piperazine co-crystal, herein denoted "resveratrol-piperazine co-crystal, Form 1", characterized by having an XRPD pattern comprising peaks at 4.48, 13.32, 16.96, 18.88, 19.16, and 22.84 °2θ±0.2 °2θ. The resveratrol-piperazine co-crystal, Form 1, can also be characterized by having an XRPD pattern comprising peaks at 4.48, 6.70, 13.32, 13.58, 15.04, 15.53, 16.96, 18.88, 19.16, 20.16, 20.41, and 22.84, °2θ±0.2 °2θ. The resveratrol-piperazine co-crystal, Form 1, is also characterized by having an XRPD pattern according to Table 1 and/or FIG. 1. The resveratrol-piperazine co-crystal, Form 1, has a fusion temperature $T_{fus}$ of 201° C.±5° C. Further, the resveratrol-piperazine co-crystal, Form 1, may be characterized by having a DSC thermogram as shown in FIG. 2.

The present document also discloses a method for producing the resveratrol-piperazine co-crystal, Form 1, as defined herein, said method comprising the steps of:
a) dispensing resveratrol in acetone or acetonitrile, optionally under stirring;
b) adding piperazine in acetone to the dispensed resveratrol of step a) thereby providing a resveratrol-piperazine mixture;
c) optionally diluting the resveratrol-piperazine mixture obtained in step b) with acetone or acetonitrile;
d) heating the resveratrol-piperazine mixture obtained in step b) or c) at a temperature within the range of from about 30° C. to about 50° C. under stirring for about 10-30 minutes thereby providing a resveratrol-piperazine suspension;
e) allowing the resveratrol-piperazine suspension obtained in step d) to settle;
f) separating a solid phase obtained in step e); and
g) drying the separated solid phase of step f).

For example, in step a) resveratrol may be dispensed in acetone and/or acetonitrile to a concentration of resveratrol of about 100 to 150 mg/ml, such as 110-140 mg/ml, 120-130 mg/ml, such as about 125 mg/ml. Step a) may be performed at room temperature (RT, 22-25° C.). The stirring in step a) may e.g. be magnetic stirring at 600-1000 rpm.

The concentration of piperazine in the acetone and/or acetonitrile in step b) may be about 10-30 mg piperazine/ml acetone, such as 15-25 mg/ml, such as about 20 mg/ml. The resveratrol-piperazine mixture may then optionally be further diluted such as 2 to 5 times by adding acetone and/or acetonitrile (step c)).

Thereafter the, optionally diluted, resveratrol-piperazine mixture is heated at a temperature within the range of from about 30° C. to about 50° C., such as about 35° C. to about 45° C., such as about 40° C., preferably under stirring, such as magnetic stirring (such as about 600-1000 RPM). The stirring step d) may be continued for about 15-20 minutes. The resulting suspension is thereafter allowed to settle, e.g. at a temperature of about 20° C. to about 25° C., such as about 22° C. to about 25° C. typically for a time period of about 5 to 15 hours, such as about 7 to 12 hours. The solid phase thereby obtained is then separated from the supernatant and left to dry, at e.g. a temperature of about 20° C. to about 25° C.

The present document also discloses a method for producing the resveratrol-piperazine co-crystal, Form 1, said method comprising the steps of:

a) dispensing resveratrol in ethanol, optionally under stirring;
b) adding piperazine in ethanol to the dispensed resveratrol of step a) thereby providing a resveratrol-piperazine mixture;
c) optionally diluting the resveratrol-piperazine mixture obtained in step b) with ethanol;
d) placing a vessel containing the mixture of step b) or c) within a further vessel containing a solvent such as tert-butyl methyl ether, wherein the mixture of the vessel and the solvent of the further vessel are kept separate from each other;
e) closing the further vessel;
f) allowing the further vessel of step e) to stand for about 7 to about 14 days, such as about 10 days;
g) optionally removing the vessel from the further vessel; and
h) allowing any solvent remaining in the vessel of step f) or step g) to evaporate.

In step a) resveratrol may be dispensed in ethanol to a resveratrol concentration to a concentration of resveratrol of about 100 to 150 mg/ml, such as 110-140 mg/ml, 120-130 mg/ml, or about 125 mg/ml. In step b), the concentration of piperazine in ethanol is about 200-600 mg/ml ethanol, such as about 300-500 mg/ml, such as about 400 mg/ml. The resveratrol-piperazine mixture may thereafter optionally be further diluted with ethanol, such as about 0.3 to 2 times dilution (step c)). Magnetic stirring, such as a rate of 600-100 rpm, may be used during steps a)-c). Step f) may e.g. be performed at a temperature of within the range of from about 20° C. to about 25° C. Evaporation step h) may be performed at a temperature of temperature of about 20° C. to about 25° C. until complete solvent evaporation is achieved.

The present document also discloses a method for producing the resveratrol-piperazine co-crystal, Form 1, said method comprising the steps of:
a) subjecting a mixture comprising resveratrol, piperazine and a solvent, such as ethanol, to grinding such as grinding in a ball mill;
b) allowing the mixture of step a) to dry thereby providing a further mixture; and
c) optionally subjecting the further mixture to further grinding.

The present document also discloses a method for producing the resveratrol-piperazine co-crystal, Form 1, said method comprising the steps of:
a) adding equimolar amounts of resveratrol and piperazine to a heating device, such as an aluminum pan or hot melt extrusion equipment;
b) heating said resveratrol and said piperazine, such as at a temperature of 100° C. or more, such as from 100° C. to 120° C., until the resveratrol and piperazine have melted and formed a melted mixture;
c) allowing said melted mixture of step b) to cool down.

The molar ratio of resveratrol and piperazine in step a) is about 1:1. The concentration of resveratrol obtained in step a) is typically about 500-750 mg/ml.

The present document is also directed to a resveratrol-piperazine co-crystal, Form 1, obtained or obtainable by any of the methods disclosed herein for producing such a co-crystal.

The present document also discloses a resveratrol-piperazine co-crystal, herein denoted "resveratrol-piperazine co-crystal, Form 2", characterized by having an XRPD pattern comprising peaks at 5.87, 12.74, 17.43, 17.70, 20.55, and 21.32 °2θ±0.2 °2θ. The resveratrol-piperazine co-crystal, Form 2, can also characterized by having an XRPD pattern comprising peaks at 5.87, 12.74, 13.09, 17.43, 17.70, 20.55, 20.74, 21.32, and 25.23 °2θ±0.2 °2θ. The resveratrol-piperazine co-crystal, Form 2, is also characterized by having an XRPD pattern according to Table 2 and/or FIG. 3. The resveratrol-piperazine co-crystal, Form 2, has a fusion temperature $T_{fus}$ of 199° C.±5° C. Further, the resveratrol-piperazine co-crystal, Form 2, may be characterized by having a DSC thermogram as shown in FIG. 4.

The present document also discloses a method for producing the resveratrol-piperazine co-crystal, Form 2, said method comprising the steps of:
a) mixing resveratrol with a solution of piperazine, such as a tetrahydrofurane solution of piperazine;
b) adding a further solvent, such as tetrahydrofurane, to the mixture obtained in step a), optionally under stirring;
c) placing a vessel containing the solution of step b) within a further vessel containing a solvent such as tert-butyl methyl ether, wherein the solution of the vessel and the solvent of the further vessel are kept separate from each other;
d) closing the further vessel;
e) allowing the further vessel of step d) to stand at a temperature within the range of from about 20° C. to about 25° C. for about 7 to about 14 days, such as about 10 days;
f) optionally removing the vessel from the further vessel; and
g) allowing any solvent remaining in the vessel of step e) or step f) to evaporate.

The concentration of resveratrol obtained in step a) is about 45-60 mg/ml, such as about 50-55 mg/ml, such as about 53 mg/ml. The concentration of piperazine obtained in step a) is about 10-30 mg/ml, such as 15-25 mg/ml, such as about 20 mg/ml. In step b), the concentration of resveratrol obtained is about 5-15 mg/ml, such as about 8-12 mg/ml, such as about 10 mg/ml. The concentration of piperazine obtained in step b) is about 10-30 mg/ml, such as about 15-25 mg/ml, such as about 20 mg/ml.

The present document also discloses a method for producing the resveratrol-piperazine co-crystal, Form 2, said method comprising the steps of:
a) subjecting a mixture comprising resveratrol, piperazine and a solvent such as tetrahydrofuran to grinding such as grinding in a ball mill;
b) allowing the mixture of step a) to dry thereby providing a further mixture; and
c) optionally subjecting the further mixture of step b) to further grinding.

The molar ratio of resveratrol and piperazine in step a) is about 1:1. The concentration of resveratrol obtained in step a) is typically about 500-750 mg/ml. The method is typically performed at room temperature, such as at 20-25° C.

The present document also discloses a resveratrol-piperazine co-crystal, Form 2, obtained or obtainable by any of the methods disclosed herein for producing such a co-crystal.

The present document also discloses a curcumin-piperazine co-crystal, herein denoted "curcumin-piperazine co-crystal, Form 1", characterized by having an XRPD pattern comprising peaks at 4.60, 9.18, 11.31, 13.12, 14.73, 16.97, 22.98, and 24.66 °2θ±0.2 °2θ. The curcumin-piperazine co-crystal, Form 1, is also characterized by having an XRPD pattern comprising peaks at 4.60, 9.18, 11.31, 12.77, 13.12, 14.73, 15.63, 16.97, 19.77, 22.98, and 24.66 °2θ±0.2 °2θ. The curcumin-piperazine co-crystal, Form 1, is also characterized by having an XRPD pattern according to Table 3 and/or FIG. 5. The curcumin-piperazine co-crystal, Form 1, has a fusion temperature $T_{fus}$ of 94° C.±5° C. Further, the curcumin-piperazine co-crystal, Form 1, may be characterized by having a DSC thermogram as shown in FIG. 6.

The present document also discloses a method for producing the curcumin-piperazine co-crystal, Form 1, as defined herein, said method comprising the steps of:
a) mixing:
  (i) a solution of curcumin, such as an acetonitrile solution of curcumin, and
  (ii) a solution of piperazine, such as an acetonitrile solution of piperazine;
b) stirring the mixture obtained in step a) at a temperature within the range of from about 40° C. to about 80° C., such as about 60° C., for a time of about 1 minute to about 60 minutes, such as 5 minutes;
c) allowing the mixture obtained in step b) to settle thereby providing a solid phase and a liquid phase;
d) separating the solid phase from the liquid phase; and
e) drying the solid phase.

The concentration of curcumin in the curcumin solution in step a)(i) is about 20-30 mg/ml, such as about 25 mg/ml. The concentration of the piperazine in the piperazine solution of step a)(ii) is about 10-30 mg/ml, such as about 15-25, such as about 20 mg/ml.

The present document also discloses a curcumin-piperazine co-crystal, Form 1, obtained or obtainable by any of the methods disclosed herein for producing such a co-crystal.

The present document also discloses a curcumin-piperazine co-crystal, herein denoted "curcumin-piperazine co-crystal, Form 2", characterized by having an XRPD pattern comprising peaks at 4.93, 9.46, 9.85, 13.98, 17.77, and 21.48 °2θ±0.2 °2θ. The curcumin-piperazine co-crystal, Form 2, is also characterized by having an XRPD pattern comprising peaks at 4.93, 9.46, 9.85, 12.11, 13.98, 14.41, 16.46, 17.77, 21.23 and 21.48 °2θ±0.2 °2θ. The curcumin-piperazine co-crystal, Form 2, is also characterized by having an XRPD pattern according to Table 4 and/or FIG. 7. The curcumin-piperazine co-crystal, Form 2, has a fusion temperature $T_{fus}$ of 87° C.±5° C. Further, the curcumin-piperazine co-crystal, Form 2, may be characterized by having a DSC thermogram as shown in FIG. 8.

The present document also discloses a method for producing the curcumin-piperazine co-crystal, Form 2, said method comprising the steps of
a) mixing:
  (i) a solution of curcumin, such as a tetrahydrofurane solution of curcumin, and
  (ii) a solution of piperazine, such as a tetrahydrofurane,
b) placing a vessel containing the mixture obtained in step a) within a further vessel containing a solvent such as hexane, wherein the mixture of the vessel and the solvent of said further vessel are kept separate from each other,
c) closing the further vessel,
d) allowing the further vessel of step c) to stand at a temperature within the range of from about 20° C. to about 25° C. for about 7 to about 14 days such as 10 days,
e) optionally removing the vessel from the further vessel, and
f) allowing any solvent remaining in the vessel of step d) or step e) to evaporate.

The concentration of curcumin in the curcumin solution of step a)(i) is about 200-300 mg/ml, such as about 225-275 mg/ml, such as about 250 mg/ml. The concentration of piperazine in the piperazine solution of step a)(ii) is about 10-30 mg/ml, such as about 15-25 mg/ml, such as about 20 mg/ml. Curcumin and piperazine are mixed in a molar ratio of about 1:1 in step a).

The present document also discloses a method for producing the curcumin-piperazine co-crystal, Form 2, said method comprising the steps of:
a) subjecting a mixture of curcumin, piperazine and a solvent such as tetrahydrofuran to grinding such as grinding in a ball mill,
b) allowing the mixture of step a) to dry thereby providing a further mixture, and
c) optionally subjecting the further mixture of step b) to further grinding.

The concentration of curcumin in the curcumin solution in step a) is about 500-750 mg/ml.

The present document is also directed to a curcumin-piperazine co-crystal, Form 2, obtained or obtainable by any of the methods disclosed herein for producing such a co-crystal.

The present document also discloses a resveratrol-piperazine-curcumin co-crystal, herein denoted "resveratrol-piperazine-curcumin co-crystal", characterized by having an XRPD pattern comprising peaks at 4.26, 11.86, 16.78, 23.46, and 25.68 °2θ±0.2 °2θ. The resveratrol-piperazine-curcumin co-crystal is also characterized by having an XRPD pattern comprising peaks at 4.26, 11.86, 12.64, 13.28, 15.66, 16.08, 16.78, 17.66, 23.46, and 25.68 °2θ±0.2 °2θ. The resveratrol-piperazine-curcumin co-crystal is also characterized by having an XRPD pattern according to Table 5 and/or FIG. 9. The resveratrol-piperazine-curcumin co-crystal has a fusion temperature $T_{fus}$ of 105° C.±5° C. Further, the resveratrol-piperazine-curcumin co-crystal may be characterized by having a DSC thermogram as shown in FIG. 10.

The present document also discloses a method for producing the resveratrol-piperazine-curcumin, said method comprising the steps of:
a) mixing, optionally under stirring:
  (i) a solution of curcumin, such as an acetone solution of curcumin, and
  (ii) a solution of resveratrol, such as an acetone solution of resveratrol, such as at a temperature within the range of about 20° C. to about 25° C.;
b) adding a solution of piperazine, such as an acetone solution of piperazine, to the mixture obtained in step a), such as at a temperature within the range of about 20° C. to about 25° C., optionally under stirring;
c) placing a vessel containing the mixture obtained in step b) within a further vessel containing a solvent such as hexane, wherein the mixture of the vessel and the solvent of the further vessel are kept separate from each other;
d) closing the further vessel;
e) allowing the further vessel of step d) to stand at a temperature within the range of from about 20° C. to about 25° C. for about 7 to about 14 days, such as about 10 days,
f) optionally removing the vessel from the further vessel; and
g) allowing any solvent remaining in the vessel of step e) or step f) to evaporate.

The concentration of curcumin in the curcumin solution of step a)(i) is about 40-60 mg/ml, such as about 45-55 mg/ml, such as about 50 mg/ml. The concentration of resveratrol in the resveratrol solution of step a)(ii) is about 110-140 mg/ml, such as about 120-130 mg/ml, such as about 125 mg/ml. The concentration of piperazine in the piperazine solution of step b) is about 10-30 mg/ml, such as about 15-25 mg/ml, such as about 20 mg/ml. The molar ratio of resveratrol:piperazine:curcumin obtained in step b) is about 1:1:1.

The present document also discloses a resveratrol-piperazine-curcumin co-crystal, obtained or obtainable by the method disclosed herein.

Instead of identifying the co-crystals of the present document via their °2θ values they can also be identified via their corresponding d [Å] values, ±0.05 Å. One Å corresponds to 0.1 nm.

Medical and Non-Medical Uses of the Co-Crystals

The co-crystals disclosed in the present document can be used in food or feed compositions. The present document is therefore also directed to a composition, such as a health supplement, food or feed composition, or a food or feed additive, comprising a resveratrol-piperazine, curcumin-piperazine and/or a resveratrol-piperazine-curcumin co-crystal as defined herein.

The resveratrol-piperazine, curcumin-piperazine and/or a resveratrol-piperazine-curcumin co-crystals may also be used as a medicament. The present document is therefore also directed to a resveratrol-piperazine, curcumin-piperazine and/or a resveratrol-piperazine-curcumin co-crystal as defined herein for use as a medicament.

The present document is also directed to a resveratrol-piperazine and/or resveratrol-piperazine-curcumin co-crystal as disclosed herein for use in the treatment and/or prevention of skin cancer, prostate cancer, colon cancer, lung cancer, breast cancer, liver cancer, heart disease, arteriosclerosis, hypertension, type II diabetes, metabolic syndrome, Alzheimer's disease, Crohn's Disease, Inflammatory Bowel Disease, autoimmune inflammatory diseases, mental disorder, ulcerative colitis, ileitis, porcine enteropathy, proliferative haemorrhagic enteropathy, and/or inflammation.

The present document is also directed to the use of a resveratrol-piperazine and/or resveratrol-piperazine-curcumin co-crystal as disclosed herein for the preparation of a medicament for the treatment and/or prevention of skin cancer, prostate cancer, colon cancer, lung cancer, breast cancer, liver cancer, heart disease, arteriosclerosis, hypertension, type II diabetes, metabolic syndrome, Alzheimer's disease, Crohn's Disease, Inflammatory Bowel Disease, autoimmune inflammatory diseases, mental disorder, ulcerative colitis, ileitis, porcine enteropathy, proliferative haemorrhagic enteropathy, and/or inflammation.

The present document is also directed to a method for treating and/or preventing skin cancer, prostate cancer, colon cancer, lung cancer, breast cancer, liver cancer, heart disease, arteriosclerosis, hypertension, type II diabetes, metabolic syndrome, Alzheimer's disease, Crohn's Disease, Inflammatory Bowel Disease, autoimmune inflammatory diseases, mental disorder, ulcerative colitis, ileitis, porcine enteropathy, proliferative haemorrhagic enteropathy, and/or inflammation comprising administering a pharmaceutically acceptable amount of a resveratrol-piperazine and/or resveratrol-piperazine-curcumin co-crystal as disclosed herein to a subject in need thereof.

The present document is further directed to a curcumin-piperazine and/or resveratrol-piperazine-curcumin co-crystal as disclosed herein for use in the treatment and/or prevention of osteoarthritis, prostate cancer, colon cancer, skin cancer, breast cancer, arteriosclerosis, digestive problems, ulcerative colitis, Crohn's Disease, Inflammatory Bowel Disease, autoimmune inflammatory diseases, dementia and/or metabolic syndrome.

The present document is also directed to the use of a curcumin-piperazine and/or resveratrol-piperazine-curcumin co-crystal as disclosed herein for the preparation of a medicament for the treatment and/or prevention of osteoarthritis, prostate cancer, colon cancer, skin cancer, breast cancer, arteriosclerosis, digestive problems, ulcerative colitis, Crohn's Disease, Inflammatory Bowel Disease, autoimmune inflammatory diseases, dementia and/or metabolic syndrome.

The present document also discloses a method for treating and/or preventing osteoarthritis, prostate cancer, colon cancer, skin cancer, breast cancer, arteriosclerosis, digestive problems, ulcerative colitis, Crohn's Disease, Inflammatory Bowel Disease, autoimmune inflammatory diseases, dementia and/or metabolic syndrome comprising administering a pharmaceutically acceptable amount of a curcumin-piperazine and/or resveratrol-piperazine-curcumin co-crystal as disclosed herein to a subject in need thereof.

The present document is also directed to a resveratrol-piperazine-curcumin co-crystal as disclosed herein for use in the treatment and/or prevention of skin cancer, prostate cancer, colon cancer, lung cancer, breast cancer, liver cancer, heart disease, arteriosclerosis, hypertension, type II diabetes, metabolic syndrome, Alzheimer's disease, Crohn's Disease, Inflammatory Bowel Disease, autoimmune inflammatory diseases, mental disorder, ulcerative colitis, ileitis, porcine enteropathy, proliferative haemorrhagic enteropathy, inflammation, osteoarthritis, arteriosclerosis, digestive problems, dementia and/or metabolic syndrome.

The present document is further directed to a resveratrol-piperazine-curcumin co-crystal as disclosed herein for use in the preparation of a medicament for the treatment and/or prevention of skin cancer, prostate cancer, colon cancer, lung cancer, breast cancer, liver cancer, heart disease, arteriosclerosis, hypertension, type II diabetes, metabolic syndrome, Alzheimer's disease, Crohn's Disease, Inflammatory Bowel Disease, autoimmune inflammatory diseases, mental disorder, ulcerative colitis, ileitis, porcine enteropathy, proliferative haemorrhagic enteropathy, inflammation, osteoarthritis, arteriosclerosis, digestive problems, dementia and/or metabolic syndrome.

Also disclosed herein is a method for treating and/or preventing skin cancer, prostate cancer, colon cancer, lung cancer, breast cancer, liver cancer, heart disease, arteriosclerosis, hypertension, type II diabetes, metabolic syndrome, Alzheimer's disease, Crohn's Disease, Inflammatory Bowel Disease, autoimmune inflammatory diseases, mental disorder, ulcerative colitis, ileitis, porcine enteropathy, proliferative haemorrhagic enteropathy, inflammation, osteoarthritis, arteriosclerosis, digestive problems, dementia and/or metabolic syndrome comprising administering a pharmaceutically acceptable amount of a resveratrol-piperazine-curcumin co-crystal as disclosed herein to a subject in need thereof.

The present document also discloses a resveratrol-piperazine, curcumin-piperazine and/or a resveratrol-piperazine-curcumin co-crystal as disclosed herein for use in the treatment and/or prevention of ileitis and/or a bacterial infection, such as in live-stock, such as swine and/or poultry.

The present document also discloses the use of a resveratrol-piperazine, curcumin-piperazine and/or a resveratrol-piperazine-curcumin co-crystal as defined herein for the preparation of a medicament for the treatment and/or prevention of ileitis and/or a bacterial infection, such as in live-stock, such as swine and/or poultry.

The present document also discloses a method for treating and/or preventing ileitis and/or a bacterial infection, such as in live-stock, such as swine and/or poultry, comprising administering a pharmaceutically acceptable amount of a resveratrol-piperazine, curcumin-piperazine and/or a resveratrol-piperazine-curcumin co-crystal as defined herein to a subject in need thereof.

The doses of the resveratrol-piperazine, curcumin-piperazine and resveratrol-curcumin-piperazine co-crystals when used for medical or non-medical purposes disclosed herein are such that the dose of the active resveratrol and/or curcumin substance is the same as commonly used for treating and/or preventing the respective condition to be treated/prevented or the respective purpose.

The resveratrol-piperazine, curcumin-piperazine and/or a resveratrol-piperazine-curcumin co-crystals disclosed herein are suitably administered orally to live-stock, such as swine or poultry. The co-crystals may be orally administered in solid form, such as powder, or in liquid form after dissolution in a suitable liquid, such as water. The co-crystals may e.g. be added to food or feed or dissolved in drinking water. The present document thus also discloses the use of a resveratrol-piperazine, curcumin-piperazine and/or a resveratrol-piperazine-curcumin co-crystal as disclosed herein as a food or feed supplement and/or a food or feed additive.

When a resveratrol-piperazine, curcumin-piperazine and/or a resveratrol-piperazine-curcumin co-crystal as disclosed herein is administered orally to live-stock, such as swine or poultry, it can increase the growth and/or improve the health of the animal to which it is administered. Without wishing to be bound by theory, this may be due to the beneficial effects resveratrol and curcumin has on the intestinal health as disclosed elsewhere herein. Such positive effects include an antibacterial effect and/or a stabilization of the gut microflora.

Resveratrol and curcumin are also known to treat and/or prevent problems associated with weaning, e.g. in live-stock such as swine and poultry. The resveratrol-piperazine, curcumin-piperazine and/or the resveratrol-piperazine-curcumin co-crystals disclosed herein may thus be administered to a subject to treat and/or prevent these kinds of problems.

The present document therefore also discloses the use of a resveratrol-piperazine co-crystal, a curcumin-piperazine co-crystal and/or a resveratrol-piperazine-curcumin co-crystal as defined herein for treating and/or preventing weaning problems, such as weaning problems in live-stock, such as in swine and/or poultry.

The present document thus also discloses a resveratrol-piperazine co-crystal, a curcumin-piperazine co-crystal and/or a resveratrol-piperazine-curcumin co-crystal as defined herein for use in the treatment and/or prevention of weaning problems, such as weaning problems in live-stock, such as in swine and/or poultry.

The present document thus also discloses the use of a resveratrol-piperazine, curcumin-piperazine and/or a resveratrol-piperazine-curcumin co-crystal as defined herein for the preparation of a medicament for the treatment and/or prevention of weaning problems, such as weaning problems in live-stock, such as in swine and/or poultry.

The present document thus also discloses a method for treating and/or preventing weaning problems, such as weaning problems in live-stock, such as in swine and/or poultry, comprising administering a pharmaceutically acceptable amount of a resveratrol-piperazine, curcumin-piperazine and/or a resveratrol-piperazine-curcumin co-crystal as herein to a subject in need thereof.

The invention will be further described in the following examples, which do not limit the scope of the invention described in the claims.

EXPERIMENTAL SECTION

Preparation of Co-Crystals of Curcumin, Resveratrol and Piperazine

All co-crystals were prepared with a starting molar ratio of the molecules to be co-crystallized of 1:1 (for the resveratrol-piperazine and curcumin-piperazine crystals) or 1:1:1 (for the resveratrol-piperazine-curcumin co-crystal).

1H NMR data supported that also the co-crystals produced all had a ratio of the compounds of 1:1 (for the resveratrol-piperazine and curcumin-piperazine crystals).

Methods of Analysis

X-Ray Powder Diffraction (XRPD)

X-ray powder diffraction patterns were obtained using a Bruker D8 Advance diffractometer equipped with a fast LynxEye detector and a Cu anode as the x-ray source (CuKα radiation, $\lambda=1.5418$, 40 kV, 40 mA). No background subtraction or curve smoothing was applied to the XRPD patterns.

It will be understood that the relative intensities of peaks may vary according to the orientation of the sample under test and on the type and setting of the instrument used so that the intensities in the XRPD traces included herein are illustrative and not intended to be used for absolute comparison.

Differential Scanning Calorimetry (DSC)

Melting properties were obtained from differential scanning calorimetry (DSC) thermograms recorded with a DSC 823e calorimeter (Mettler-Toledo GmbH. Switzerland), under nitrogen flow (80 ml/min). Samples were heated in pierced 40 μl aluminium pans at a 10° C./min constant heating rate.

Dissolution Rate Determination

In situ dissolution experiments were performed with a μDISS Profiler apparatus (pION Inc., MA, USA). The system consists of an integrated diode array spectrophotometer connected to a fiber optic UV probe located directly in the reaction vessel (20 ml scintillation vial) and measures the concentration as a function of time, without filtering the solution. Measurement of the dissolution kinetics was carried out at 220 nm and 270 nm, which are optimal for the UV detection of resveratrol and curcumin, respectively. The concentrations of the compounds in the dissolution media (water, buffer pH=4, pH=6) were calculated by means of a standard curve.

Example 1: Resveratrol-Piperazine Co-Crystal, Form 1

Experimental Protocols—all Resulting in Resveratrol-Piperazine Co-Crystal, Form 1

A) Crystallization from Solution, Alternative 1

25 mg resveratrol was dispensed in 200 μl acetone at room temperature (RT, 22-25° C.) under magnetic stirring (600-1000 RPM). Next, 470 μl solution of piperazine in acetone, of concentration 20 mg piperazine/ml acetone was added. The mixture was further diluted by adding 1800 μl acetone followed by heating at 40° C. under magnetic stirring (600-1000 RPM) for 15-20 minutes. The resulting suspension was allowed to settle at RT overnight, then separated from the supernatant and left to dry at ambient conditions.

B) Crystallization from Solution, Alternative 2

25 mg resveratrol was dispensed in 200 μl ethanol at room temperature (RT, 22-25° C.) under magnetic stirring (600-1000 RPM). Next, 24 μl solution of piperazine in ethanol, of concentration 400 mg piperazine/ml EtOH was added. An additional 100 μl ethanol was added under magnetic stirring (600-1000 RPM) to allow for complete dissolution. The 4 ml glass vial containing the above solution was inserted opened in a 20 ml glass vial containing 1950 μl tert-butyl methyl ether (TBME). The 20 ml vial was subsequently closed and kept at RT for 10 days. Then, the 20 ml vial was opened, the 4 ml vial was extracted and left opened at RT, allowing for complete solvent evaporation.

C) Grinding Method 20 mg resveratrol and 7.62 mg piperazine were added in a ball-mill reactor together with 40 μl ethanol, followed by grinding at a frequency of 30 Hz for 120 minutes. The resulting mixture was allowed to dry at ambient conditions for 12 h, and then it was recovered and homogenized by gentle manual grinding.

D) Upscaling of Grinding Method, 400 mg

It was also tested whether the grinding method could be scaled up. Thus, 400 mg of resveratrol was used as a starting material in the method and piperazine in an amount of 151-152 mg. The other conditions during the preparation were the same.

E) Synthesis of Up to 100 g Batches Via Grinding Method

Equimolar quantities of resveratrol (RESV) and piperazine (PIP) were weighted and added to a ~0.5 L planetary ball mill steel container. Ethanol was then added. The reaction mixture was stirred at 350 RPM and 20° C. for different periods, ranging from 0.5 to 4 h. The exact quantities used are presented in Table 6. The ratio EtOH to RESV was varied between 0.6-1.4 ml/g.

TABLE 6

Experimental protocol upscaling of preparation of the resveratrol-piperazine co-crystal, Form 1

| Name | mass RESV (g) | mass PIP (g) | EtOH (ml) | RESV/PIP (mol/mol) | EtOH/RESV (ml/g) | Steel Balls* |
|---|---|---|---|---|---|---|
| RP1 | 25.0 | 9.53 | 15 | 1.0 | 0.60 | 4/7/38 |
| RP2 | 18.24 | 6.95 | 25 | 1.0 | 1.37 | 4/7/38 |
| RP3 | 101.72 | 38.8 | 100 | 1.0 | 0.98 | 7/12/38 |
| RP4 | 102.0 | 38.8 | 100 | 1.0 | 0.98 | 7/12/38 |

*Expressed as the number of balls with 2 cm/1 cm/0.5 cm diameter, respectively.

Figure 12:
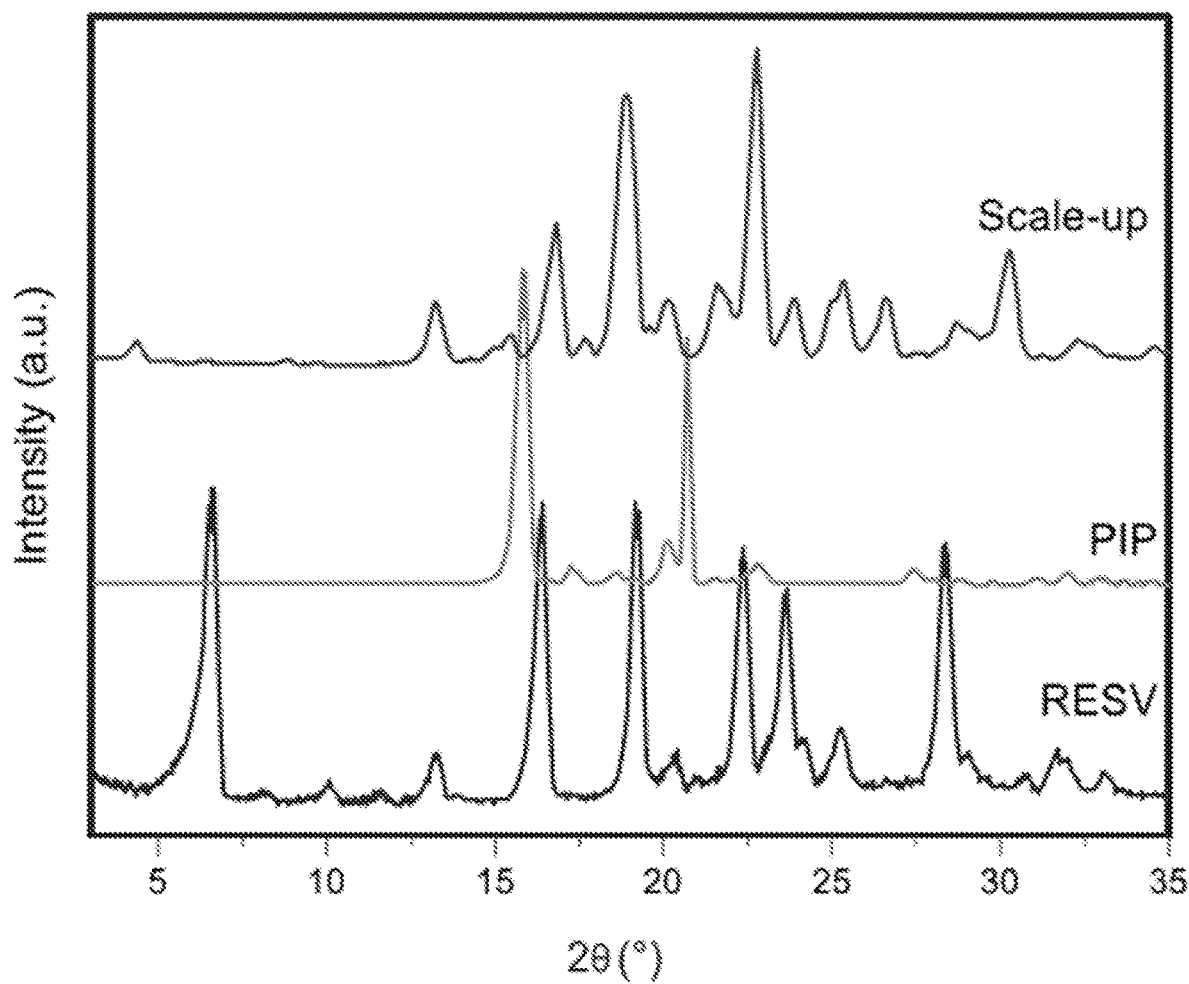
FIG. 12. X-ray powder diffraction pattern of the resveratrol-piperazine co-crystal, Form 1, prepared by the grinding method in batches up to 600 g. The X-ray powder diffraction patterns of the components (resveratrol and piperazine) are included for comparison.

Samples were withdrawn and analyzed by XRPD, see FIG. 12.

F) Synthesis of 600 g Batches Via Grinding Method

Equimolar quantities of resveratrol (RESV) and piperazine (PIP) were weighted and added to a ~25 L mixer mill steel container equipped with stainless steel knives in cross position. Ethanol was then added (0.98 ml/g). The reaction mixture (600 g load) was stirred at 750 RPM for 1 h. Samples were withdrawn and analyzed by XRPD, see FIG. 12

G) Melting Method

Small, equimolar quantities of resveratrol (1.88 mg) and piperazine (0.78 mg) were heated in pierced 40 μl aluminium pan at a 10° C./min constant heating rate, similar to the DSC analysis.

Figure 17:
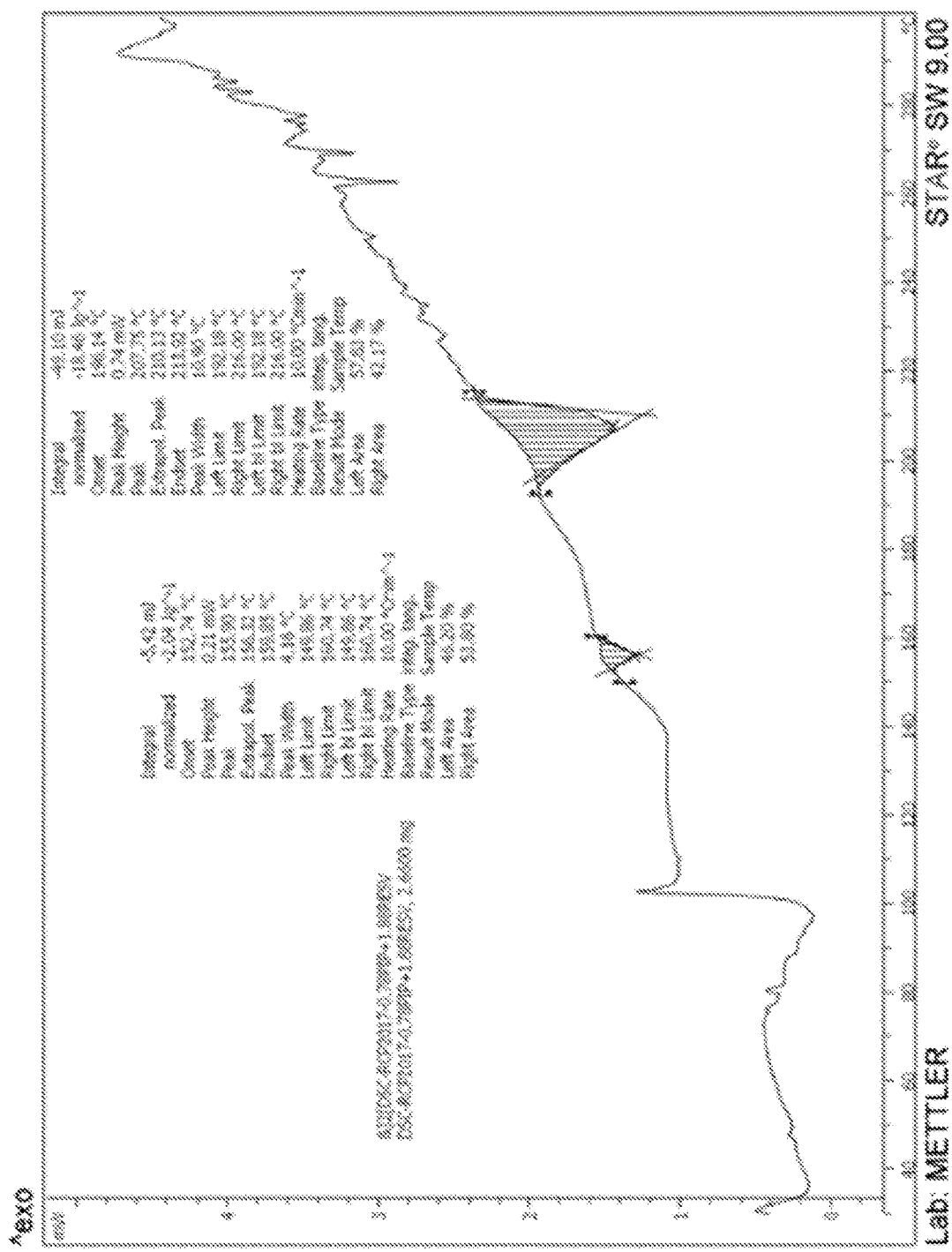
FIG. 17. DSC trace of the melting method for producing the resveratrol-piperazine co-crystal, Form 1, showing the eutectic melting followed by crystallization (endotherm and exotherm events at about 100° C.), a solid-solid transformation (small endotherm at about 153° C.) and co-crystal melting (endotherm at about 200° C., coincides with the resveratrol-piperazine co-crystal, Form 1, melting in FIG. 2).

The result indicated that resveratrol-piperazine co-crystal, Form 1, is obtained by melting equimolar amounts of the dry components (FIG. 17).

Characterization of Resveratrol-Piperazine Co-Crystal, Form 1

FIG. 1a shows the X-ray powder diffraction pattern of the resveratrol-piperazine, Form 1 co-crystal. FIG. 1b shows an overlay of the XRPD pattern for the resveratrol-piperazine, Form 1 co-crystal with the resveratrol-piperazine, Form 1 co-crystal prepared in the upscaled grinding method under D) above. As can be seen in this figure, the patterns are the same. Thus, it was thereby demonstrated that the grinding method was a successful method for preparing larger amounts of the resveratrol-piperazine, Form 1 co-crystal. FIG. 2 shows the DSC thermogram of the resveratrol-piperazine co-crystal, Form 1.

TABLE 1

X-ray powder reflections (up to 33° 2θ) and intensities (normalized) of the resveratrol-piperazine co-crystal, Form 1. The value 2θ [°] represents the diffraction angle in degrees and the value d [Å] represents the specified distances in Å between the lattice planes.

| 2θ [°] | d [Å] | I/I$_o$ [%] |
|---|---|---|
| 4.48 | 19.69 | 21 |
| 6.70 | 13.19 | 14 |
| 8.90 | 9.92 | 12 |
| 13.32 | 6.64 | 38 |
| 13.58 | 6.52 | 23 |
| 14.39 | 6.15 | 12 |
| 15.04 | 5.89 | 17 |
| 15.53 | 5.70 | 23 |
| 16.59 | 5.34 | 21 |
| 16.96 | 5.22 | 68 |
| 17.77 | 4.99 | 20 |
| 18.88 | 4.70 | 67 |
| 19.16 | 4.63 | 83 |
| 19.55 | 4.54 | 16 |
| 19.69 | 4.50 | 20 |
| 20.16 | 4.40 | 28 |
| 20.41 | 4.35 | 28 |
| 21.68 | 4.10 | 30 |
| 22.04 | 4.03 | 27 |
| 22.55 | 3.94 | 24 |
| 22.84 | 3.89 | 100 |
| 23.00 | 3.86 | 54 |
| 23.69 | 3.75 | 22 |
| 24.02 | 3.70 | 31 |
| 25.05 | 3.55 | 26 |
| 25.46 | 3.50 | 32 |
| 25.80 | 3.45 | 14 |
| 26.29 | 3.39 | 15 |
| 26.74 | 3.33 | 25 |
| 28.42 | 3.14 | 18 |
| 28.77 | 3.10 | 19 |
| 29.18 | 3.06 | 16 |
| 29.64 | 3.01 | 16 |
| 30.08 | 2.97 | 19 |
| 30.40 | 2.94 | 34 |
| 31.79 | 2.81 | 12 |
| 32.42 | 2.76 | 14 |
| 32.79 | 2.73 | 13 |

Particularly characteristic peaks for the resveratrol-piperazine co-crystal, Form 1, in the X-ray powder diffractogram were found to be: d=19.69±0.05 Å, d=6.64±0.05 Å, d=5.22±0.05 Å, d=4.70±0.05 Å, d=4.63±0.05 Å, d=3.89±0.05 Å.

The resveratrol-piperazine co-crystal, Form 1, was found to be characterized by a fusion temperature of T$_{fus}$ (onset) =201° C.±5° C., which occurred during thermal analysis using DSC. The resveratrol-piperazine co-crystal, Form 1, was shown to be physically stable on storage under accelerated conditions (40° C., 75% relative humidity for at least 1 week). Further, it showed an increased aqueous solubility at pH=4 and pH=6 compared to resveratrol (in the range of 65-100 micrograms/ml for the co-crystals versus 30 micrograms/ml in the case of resveratrol). This difference is very relevant for the intestinal absorption profile of resveratrol after administration to a subject as drugs and nutrients are absorbed primarily in the small intestine. The small intestine is made up by duodenum, jejunum and ileum. In humans, the pH is rapidly changes from highly acidic in the stomach to about pH 6 in the duodenum. The pH gradually increases in the small intestine from pH 6 to about pH 7.4 in the terminal ileum. An increased solubility of an orally administered substance at these higher pH values is therefore of great importance for its absorption profile in small intestine.

Solubility and Dissolution Rate of Resveratrol and Resveratrol-Piperazine Co-Crystal, Form 1

Dissolution of Resveratrol and Resveratrol-Piperazine Co-Crystal, Form 1, at pH 6

The calibration curve was obtained in a mixture of ethanol and water at 8/2 (vol/vol). Stock solutions of resveratrol and resveratrol-piperazine co-crystal, Form 1, respectively, were prepared at 10 mg/ml. The calibration was performed in a 20 ml volume.

The dissolution was performed in 25 mM phosphate buffer ($Na_2HPO_4/KH_2PO_4$) at pH 6, at a concentration of 1 mg/ml resveratrol and resveratrol-piperazine co-crystal, Form 1, respectively. An amount of 20 mg of each compound was dispensed in 20 ml volume of buffer. The process was monitored for 90 minutes. The corresponding results are displayed in FIG. 13.

Dissolution of Resveratrol and Resveratrol-Piperazine Co-Crystal, Form 1, at pH 4

The calibration was performed in a mixture of ethanol and sodium acetate buffer pH 4.0 at 8/2 (vol/vol) and final concentration of 25 mM sodium acetate. Stock solutions of resveratrol and resveratrol-piperazine co-crystal, Form 1, respectively, were prepared at 10 mg/ml in the solvent mixture. The calibration was performed in 20 ml volume.

The dissolution was performed in 25 mM sodium acetate buffer at pH 4.0, at a concentration of 1 mg/ml resveratrol and resveratrol-piperazine co-crystal, Form 1 (RP1), respectively. An amount of 20 mg compound was dispensed in 20 ml volume of buffer. The process was monitored for 90 minutes. The corresponding results are displayed in FIG. 14.

Figure 13:
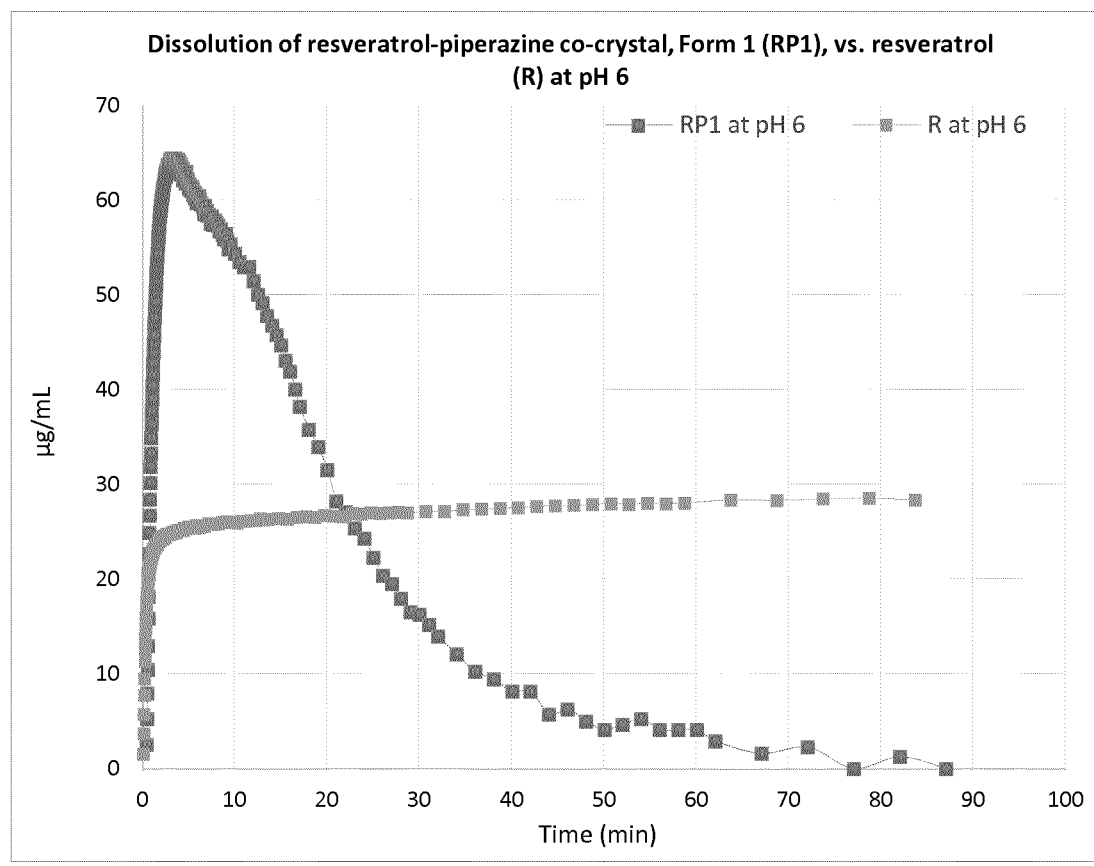
FIG. 13. Dissolution rate for resveratrol-piperazine co-crystal, Form 1, and resveratrol at pH 6.
Figure 14:
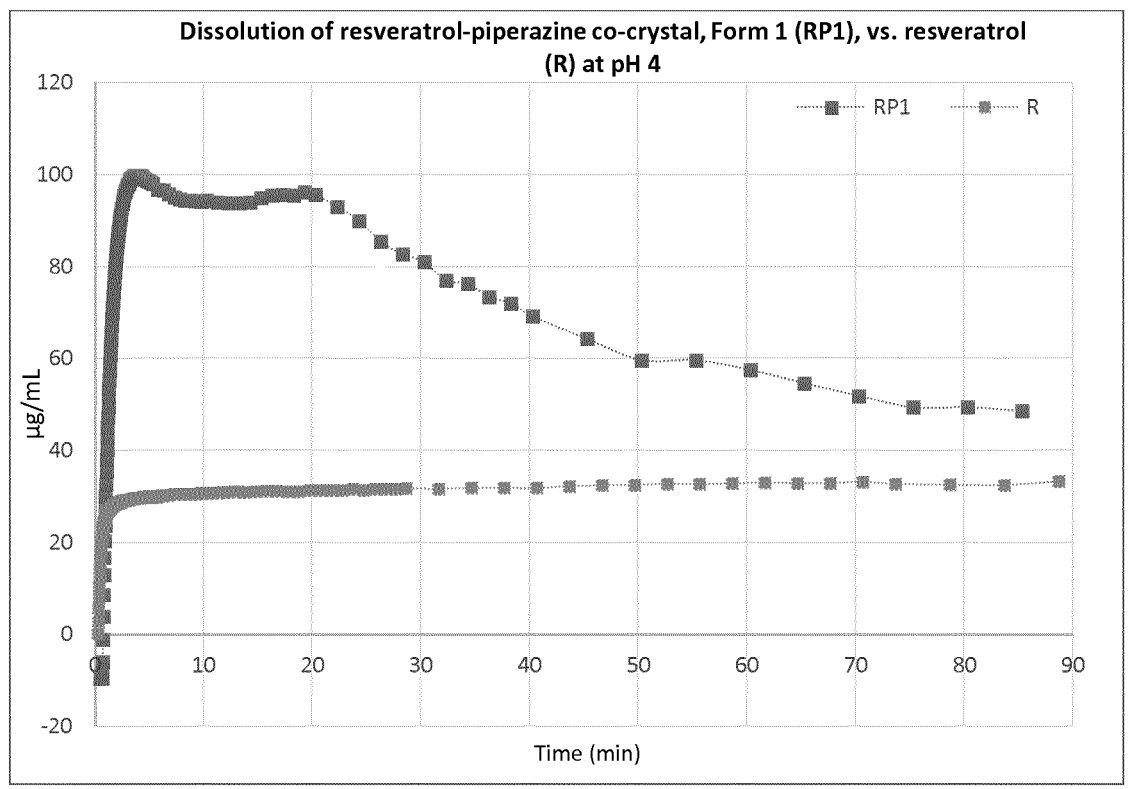
FIG. 14. Dissolution rates for resveratrol-piperazine co-crystal, Form 1, and resveratrol at pH 4.

The results show that resveratrol-piperazine co-crystal, Form 1, solubility at pH 4 is three times higher than that of resveratrol. The pH 4 buffer appears to maintain Form 1 in solution longer than in the case of the pH 6 buffer (FIG. 14 and FIG. 13, respectively).

Example 2: Resveratrol-Piperazine Co-Crystal, Form 2

Experimental Protocols—All Resulting in Resveratrol-Piperazine Co-Crystal, Form 2

A) Crystallization from Solution 25 mg resveratrol was mixed at room temperature (RT, 22-25° C.) with 470 μl solution of piperazine in tetrahydrofuran (THF), of concentration 20 mg piperazine/ml THF. An additional 1900 μl THF was added at RT under magnetic stirring (600-1000 RPM) to allow for complete dissolution. The 4 ml glass vial containing the above solution was inserted opened in a 20 ml glass vial containing 5 ml tert-butyl methyl ether (TBME). The 20 ml vial was subsequently closed and kept at RT for 10 days. Then, the 20 ml vial was opened, the 4 ml vial was extracted and left opened at RT, allowing for complete solvent evaporation.

B) Grinding Method 20 mg resveratrol and 7.62 mg piperazine were added in a ball-mill reactor together with 40 μl tetrahydrofuran (THF), followed by grinding at a frequency of 30 Hz for 120 minutes. The resulting mixture was allowed to dry at ambient conditions for 12 h, after which it was recovered and homogenized by gentle manual grinding.

Characterization of Resveratrol-Piperazine Co-Crystal, Form 2

Figure 3:
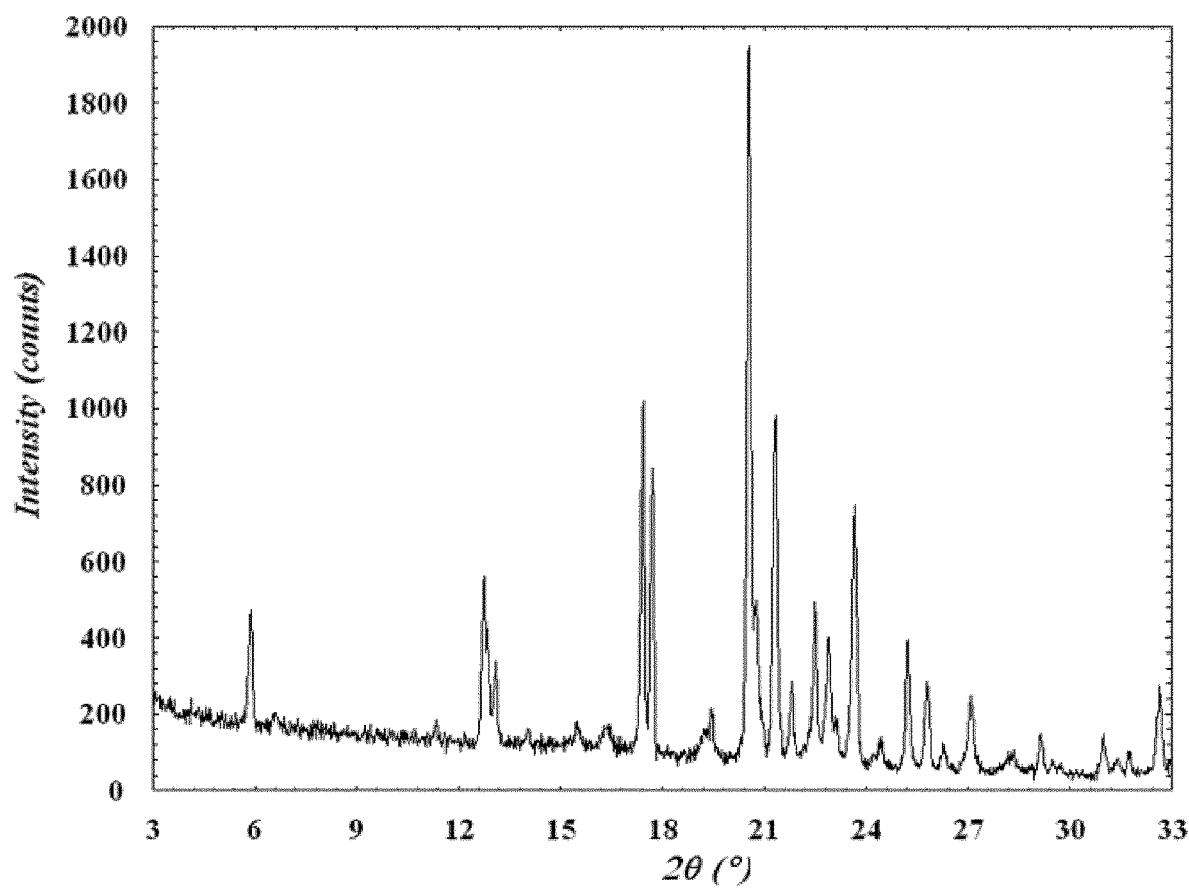
FIG. 3. X-ray powder diffraction pattern of the resveratrol-piperazine co-crystal, Form 2.
Figure 4:
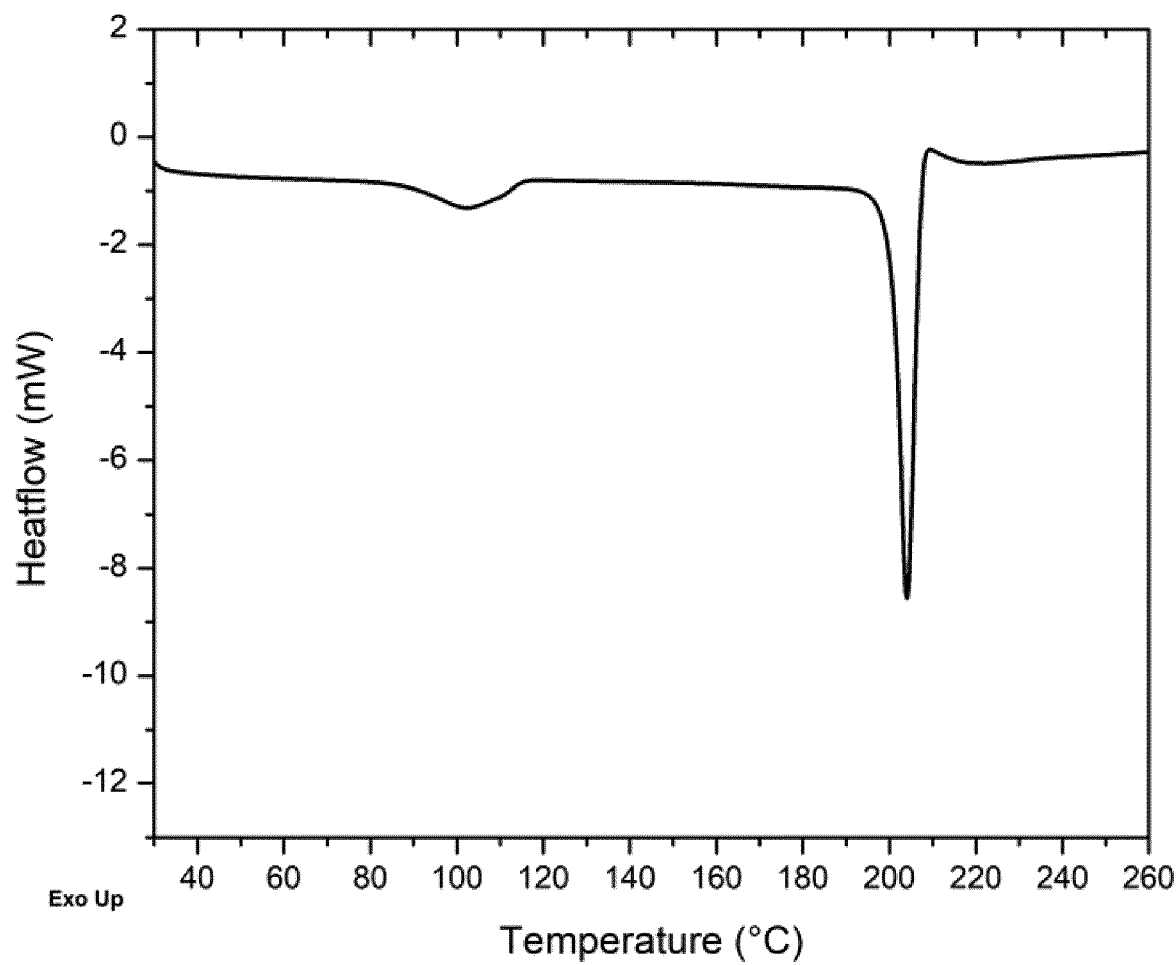
FIG. 4. DSC thermogram of the resveratrol-piperazine co-crystal, Form 2.

FIG. 3 shows the X-ray powder diffraction pattern of the resveratrol-piperazine co-crystal, Form 2. FIG. 4 shows the DSC thermogram of the resveratrol-piperazine co-crystal, Form 2.

TABLE 2

X-ray powder reflections (up to 33° 2θ) and intensities (normalized) of the resveratrol-piperazine co-crystal, Form 2. The value 2θ [°] represents the diffraction angle in degrees and the value d [Å] represents the specified distances in Å between the lattice planes.

| 2θ [°] | d [Å] | $I/I_o$ [%] |
|---|---|---|
| 5.87 | 15.03 | 24 |
| 12.74 | 6.94 | 29 |
| 13.09 | 6.76 | 17 |
| 14.05 | 6.30 | 8 |
| 15.49 | 5.72 | 9 |
| 17.43 | 5.08 | 52 |
| 17.70 | 5.01 | 43 |
| 19.45 | 4.56 | 10 |
| 20.55 | 4.32 | 100 |
| 20.74 | 4.28 | 25 |
| 21.32 | 4.16 | 49 |
| 21.80 | 4.07 | 15 |
| 22.49 | 3.95 | 25 |
| 22.90 | 3.88 | 19 |
| 23.10 | 3.85 | 8 |
| 23.65 | 3.76 | 38 |
| 24.43 | 3.64 | 7 |
| 25.23 | 3.53 | 20 |
| 25.81 | 3.45 | 14 |
| 26.27 | 3.39 | 6 |
| 27.09 | 3.29 | 13 |
| 29.14 | 3.06 | 7 |
| 30.98 | 2.88 | 7 |
| 32.64 | 2.74 | 12 |

Particularly characteristic peaks in the X-ray powder diffractogram were found to be: d=15.03±0.05 Å, d=6.94±0.05 Å, d=5.08±0.05 Å, d=5.01±0.05 Å, d=4.32±0.05 Å, d=4.16±0.05 Å

The resveratrol-piperazine co-crystal, Form 2 was found to be characterized by a fusion temperature of $T_{fus}$ (onset) =199° C.±5° C., which occurred during thermal analysis using DSC.

The DSC thermogram was additionally found to be characterized by a broad, weak endothermic signal observed at approximately 100° C., indicating loss of solvent.

Example 3: Curcumin-Piperazine Co-Crystal, Form 1

A) Crystallization from Solution 25 mg curcumin was dissolved in 1000 μl acetonitrile at 60° C. under magnetic stirring (1000 RPM). Next, 290 μl solution of piperazine in acetonitrile, of concentration 20 mg piperazine/ml acetonitrile was added. After briefly (up to 5 minutes) stirring at 60° C., the mixture was allowed to settle at room temperature (RT) overnight. The resulting precipitate was separated from the supernatant and left to dry at ambient conditions.

Characterization of Curcumin-Piperazine Co-Crystal, Form 1

Figure 5:
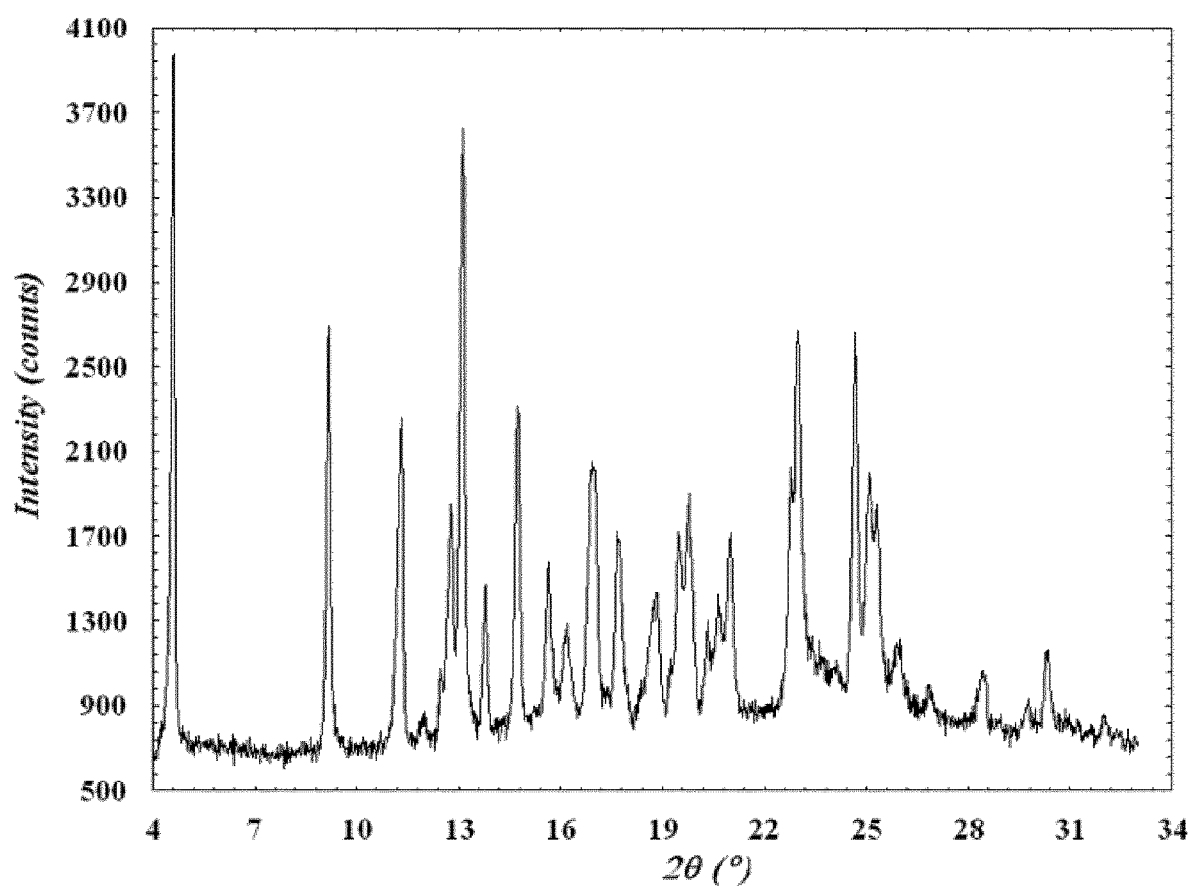
FIG. 5. X-ray powder diffraction pattern of the curcumin-piperazine co-crystal, Form 1.
Figure 6:
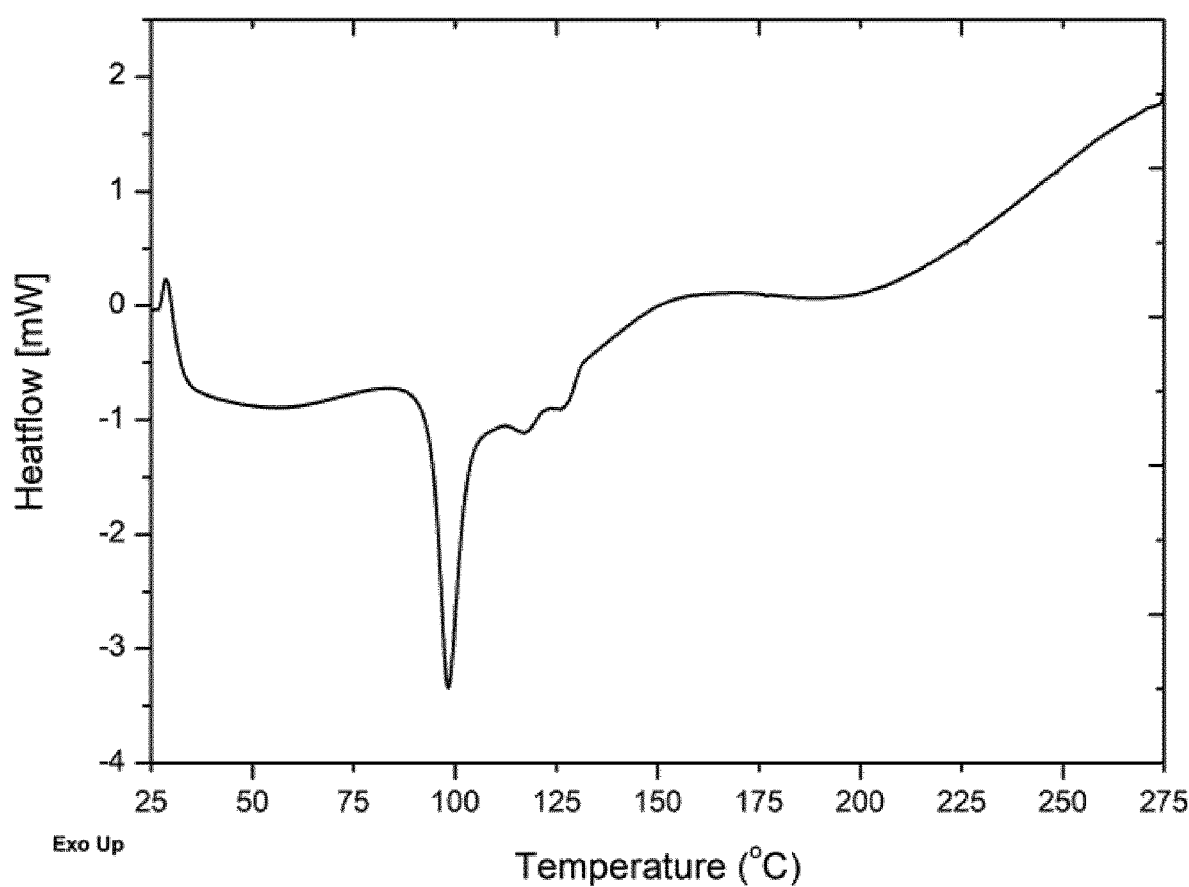
FIG. 6. DSC thermogram of the curcumin-piperazine co-crystal, Form 1.

FIG. 5 shows the X-ray powder diffraction pattern of the curcumin-piperazine co-crystal, Form 1. FIG. 6 shows the DSC thermogram of the curcumin-piperazine co-crystal, Form 1.

Particularly characteristic peaks in the X-ray powder diffractogram were found to be: d=19.18±0.05 Å, d=9.63±0.05 Å, d=7.82±0.05 Å, d=6.74±0.05 Å, d=6.01±0.05 Å, d=5.22±0.05 Å, d=3.87±0.05 Å, d=3.61±0.05 Å.

The curcumin-piperazine co-crystal, Form 1 was found to be characterized by a fusion temperature of $T_{fus}$ (onset)=94° C.±5° C., which occurred during thermal analysis using DSC.

The curcumin-piperazine co-crystal, Form 1 was found to be physically stable on storage under accelerated conditions (40° C., 75% relative humidity for at least 1 week). Further it showed an increased aqueous solubility compared to curcumin (by visual observation when suspending equal powder amounts in water; curcumin was floating on the surface and the water did not colour, while the co-crystal entered in solution and water became dark-coloured).

TABLE 3

X-ray powder reflections (up to 33° 2θ) and intensities (normalized) of the Curcumin- Piperazine co-crystal, Form 1. The value 2θ [°] represents the diffraction angle in degrees and the value d [Å] represents the specified distances in Å between the lattice planes.

| 2θ [°] | d [Å] | I/I$_o$ [%] |
|---|---|---|
| 4.60 | 19.18 | 100 |
| 9.18 | 9.63 | 68 |
| 11.31 | 7.82 | 56 |
| 12.49 | 7.08 | 26 |
| 12.77 | 6.92 | 46 |
| 13.12 | 6.74 | 91 |
| 13.78 | 6.42 | 37 |
| 14.73 | 6.01 | 58 |
| 15.63 | 5.67 | 40 |
| 16.18 | 5.47 | 32 |
| 16.97 | 5.22 | 51 |
| 17.71 | 5.00 | 42 |
| 18.84 | 4.71 | 36 |
| 19.50 | 4.55 | 43 |
| 19.77 | 4.49 | 46 |
| 20.35 | 4.36 | 32 |
| 20.65 | 4.30 | 35 |
| 20.98 | 4.23 | 43 |
| 22.78 | 3.90 | 50 |
| 22.98 | 3.87 | 67 |
| 24.66 | 3.61 | 67 |
| 25.09 | 3.55 | 50 |
| 25.31 | 3.52 | 46 |
| 25.93 | 3.43 | 30 |
| 26.84 | 3.32 | 25 |
| 28.42 | 3.14 | 27 |
| 29.75 | 3.00 | 23 |
| 30.32 | 2.95 | 28 |

Example 4: Curcumin-Piperazine Co-Crystal, Form 2

Experimental Protocols—Both Resulting in Curcumin-Piperazine Co-Crystal—Form 2

A) Crystallization from Solution 25 mg curcumin was dissolved in 100 μl tetrahydrofuran (THF) at room temperature (RT, 22-25° C.), under magnetic stirring (600-1000 RPM). Next, 290 μl of piperazine solution in THF of concentration 20 mg piperazine/ml THF was added. The 4 ml glass vial containing the above solution was inserted opened in a 20 ml glass vial containing 1500 μl hexane. The 20 ml vial was subsequently closed and kept at RT for 10 days. Then, the 20 ml vial was opened, the 4 ml vial was extracted and left opened at RT, allowing for complete solvent evaporation.

B) Grinding Method 30 mg curcumin and 7.1 mg piperazine were added in a ball-mill reactor together with 40 μl tetrahydrofuran (THF), followed by grinding at a frequency of 30 Hz for 120 minutes. The resulting mixture was allowed to dry at ambient conditions for 12 h, then it was recovered and homogenized by gentle manual grinding.

Characterization of Curcumin-Piperazine Co-Crystal, Form 2

Figure 7:
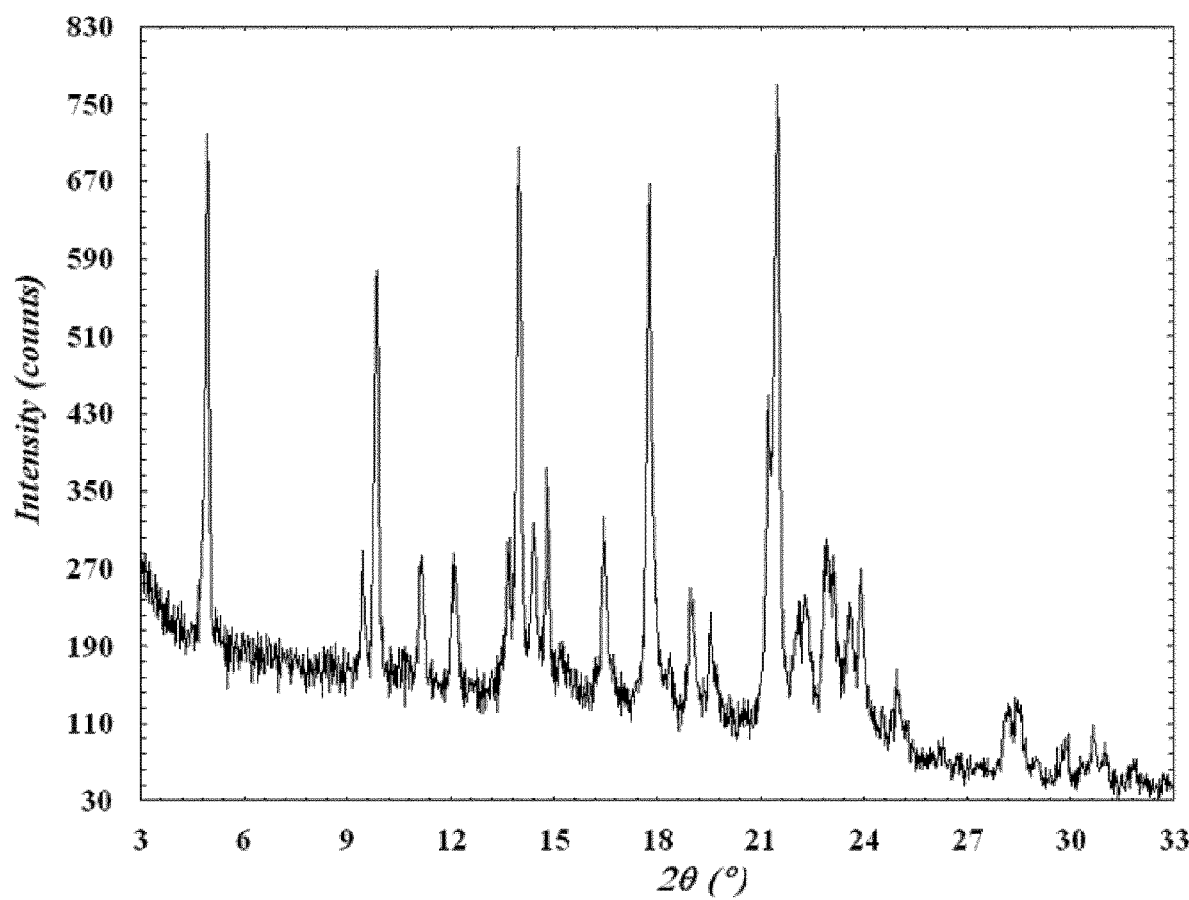
FIG. 7. X-ray powder diffraction pattern of the curcumin-piperazine co-crystal, Form 2.
Figure 8:
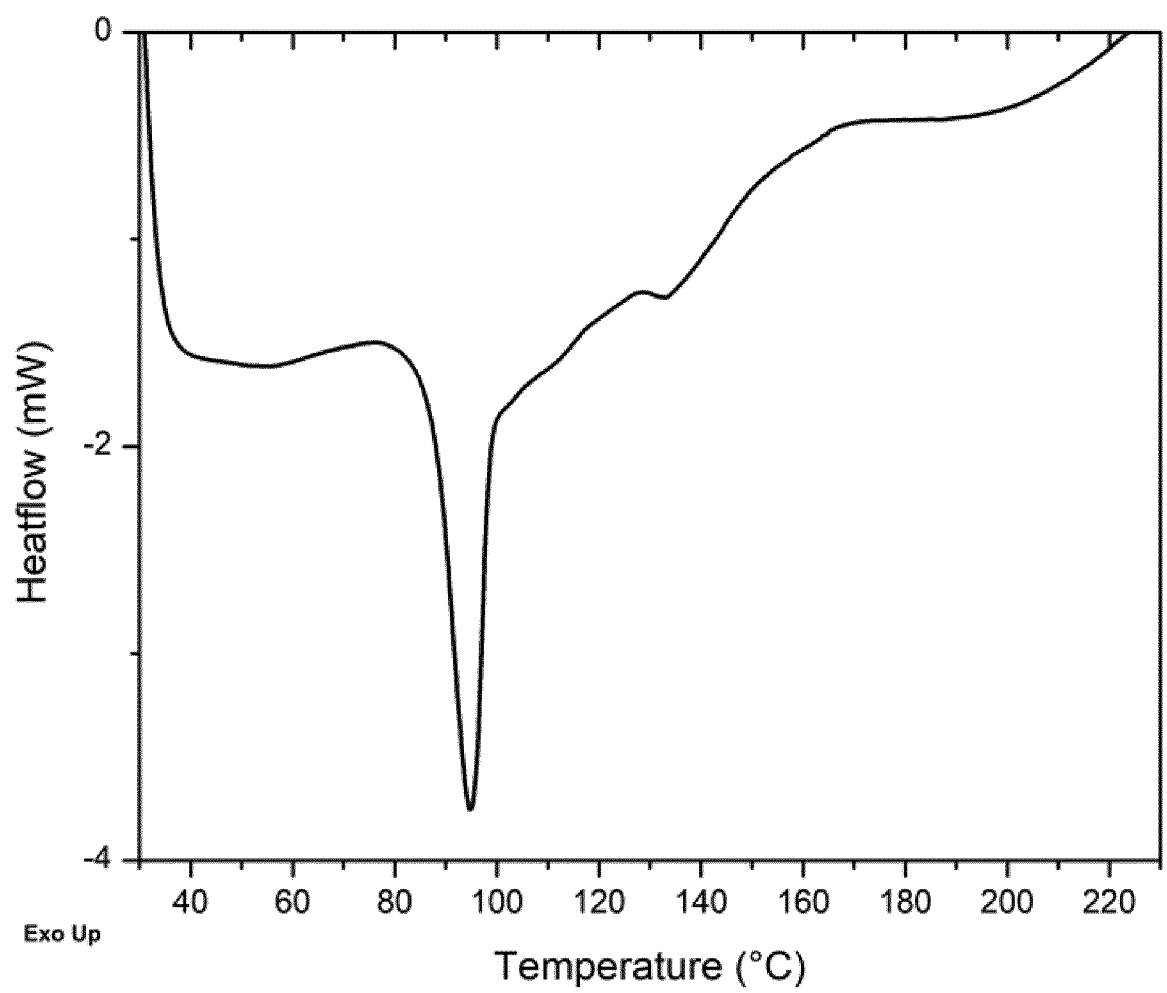
FIG. 8. DSC thermogram of the curcumin-piperazine co-crystal, Form 2.

FIG. 7 shows the X-ray powder diffraction pattern of the curcumin-piperazine co-crystal, Form 2. FIG. 8 shows the DSC thermogram of the curcumin-piperazine co-crystal, Form 2.

Particularly characteristic peaks in the X-ray powder diffractogram were found to be: d=17.90±0.05 Å, d=9.35±0.05 Å, d=8.97±0.05 Å, d=6.33±0.05 Å, d=4.99±0.05 Å, d=4.13±0.05 Å.

The curcumin-piperazine co-crystal, Form 2 was found to be characterized by a fusion temperature of $T_{fus}$ (onset)=87° C.±5° C., which occurred during thermal analysis using DSC.

TABLE 4

X-ray powder reflections (up to 33° 2θ) and intensities (normalized) of the curcumin-piperazine co-crystal, Form 2. The value 2θ [°] represents the diffraction angle in degrees and the value d [Å] represents the specified distances in Å between the lattice planes.

| 2θ [°] | d [Å] | I/I$_o$ [%] |
|---|---|---|
| 4.93 | 17.90 | 93 |
| 9.46 | 9.35 | 36 |
| 9.85 | 8.97 | 75 |
| 11.15 | 7.93 | 35 |
| 12.11 | 7.30 | 31 |
| 13.67 | 6.47 | 36 |
| 13.98 | 6.33 | 89 |
| 14.41 | 6.14 | 39 |
| 14.81 | 5.98 | 46 |
| 16.46 | 5.38 | 40 |
| 17.77 | 4.99 | 87 |
| 18.98 | 4.67 | 31 |
| 19.56 | 4.54 | 27 |
| 21.23 | 4.18 | 57 |
| 21.48 | 4.13 | 100 |
| 22.10 | 4.02 | 28 |
| 22.29 | 3.99 | 32 |
| 22.93 | 3.87 | 37 |
| 23.11 | 3.85 | 36 |
| 23.60 | 3.77 | 30 |
| 23.91 | 3.72 | 35 |
| 24.97 | 3.56 | 18 |
| 28.19 | 3.16 | 17 |
| 28.45 | 3.14 | 17 |

Solubility and Dissolution Rate of Curcumin and Curcumin-Piperazine Co-Crystal, Form 2 (CP2)

The calibration was performed in a mixture of tetrahydrofuran and water at 4/6 (vol/vol). Stock solutions of curcumin and curcumin-piperazine co-crystal, Form 2, respectively, were prepared at 10 mg/ml in THF/water (4/6). The calibration was performed in 20 ml volume at 1, 2, 5, 10, 20, 40, 60 micrograms/ml.

The dissolution was performed at a concentration of 1 mg/ml curcumin and curcumin-piperazine co-crystal, Form 2, respectively, in water. An amount of 20 mg compound was dispensed in 20 ml water. The process was monitored for 120 minutes. The corresponding results are displayed in FIG. 15.

Figure 15:
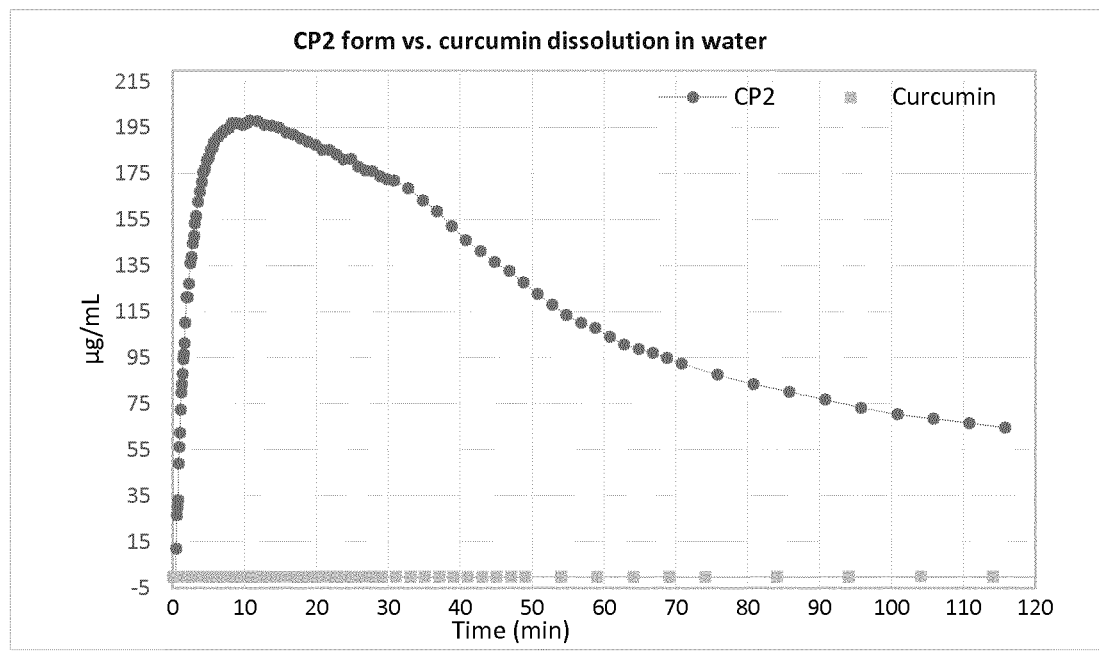
FIG. 15. Dissolution rates for curcumin and curcumin-piperazine co-crystal, Form 2 (CP2), in water.
Figure 16:
FIG. 16. Images of the curcumin and curcumin-piperazine co-crystal, Form 2 (CP2) (left) and curcumin (right) solids dispensed in water.

The curcumin-piperazine co-crystal, Form 2, has a significantly increased solubility in comparison with curcumin (which is practically insoluble in water, FIG. 16). The CP2 solubility appears to diminish gradually over time probably due to the partial CP2 dissociation in curcumin and piperazine (FIG. 15).

Example 5: Resveratrol-Piperazine-Curcumin Co-Crystal

Experimental Protocol—Resveratrol-Piperazine-Curcumin Co-Crystal (as Single Form)

Two separated solutions were prepared at room temperature (RT, 22-25° C.) as follows: 25 mg of curcumin in 500 μl acetone and 15.5 mg of resveratrol in 124 μl acetone. The two solutions were mixed under magnetic stirring at RT (600-1000 RPM). Next, 290 μl of piperazine solution in acetone, of concentration 20 mg piperazine/ml acetone was added under stirring at RT. The 4 ml glass vial containing the above solution mix was inserted opened in a 20 ml glass vial containing 3 ml hexane. The 20 ml vial was subsequently closed and kept at RT for 7 days. Then, the 20 ml vial was opened, the 4 ml vial was extracted and left opened at RT, allowing for complete solvent evaporation.

Characterization of the Resveratrol-Piperazine-Curcumin Co-Crystal

Figure 9:
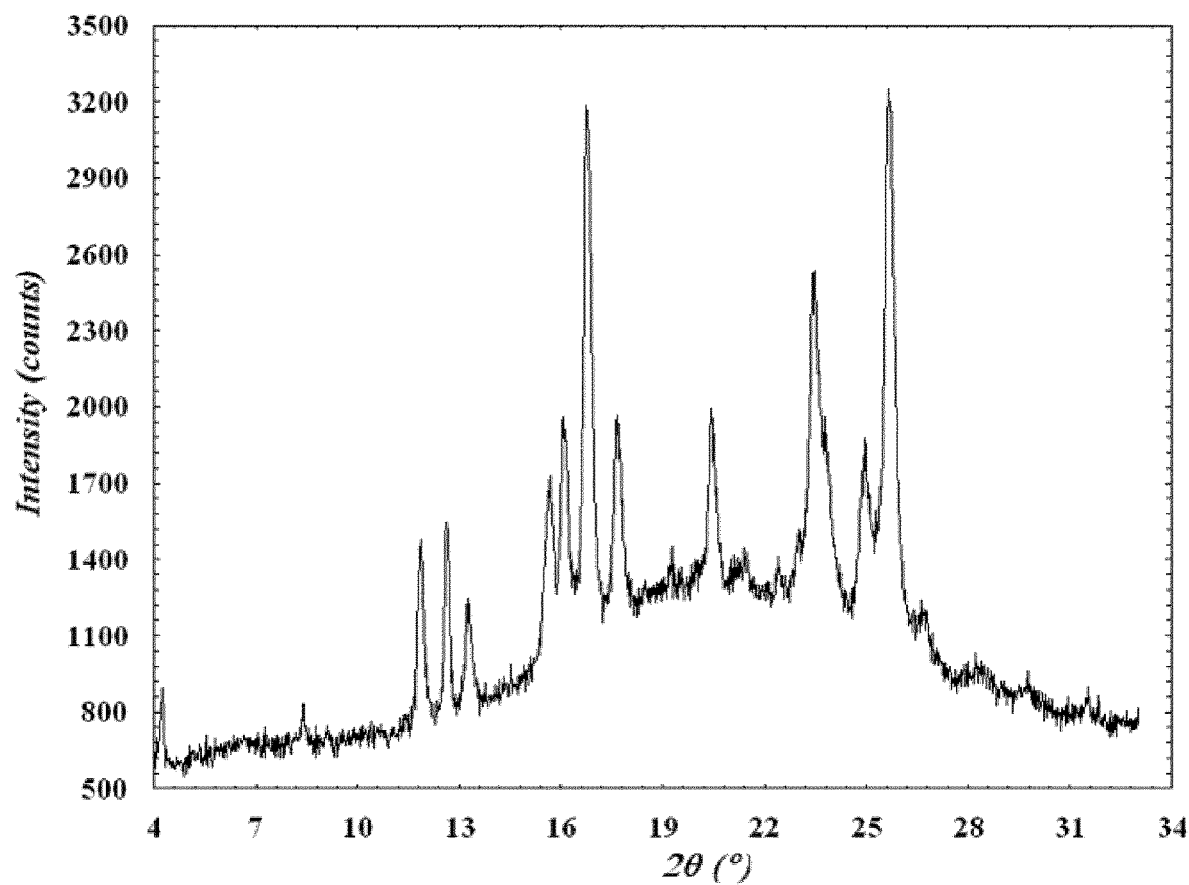
FIG. 9. X-ray powder diffraction pattern of the resveratrol-piperazine-curcumin co-crystal.
Figure 10:
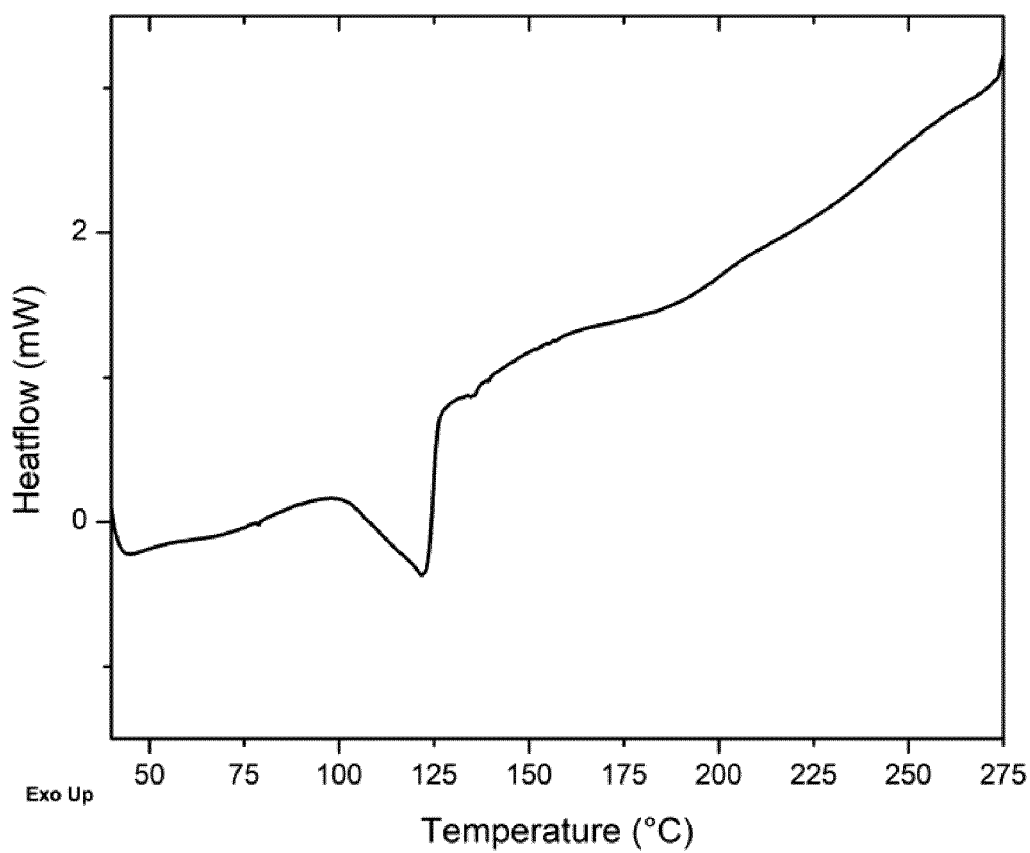
FIG. 10. DSC thermogram of the resveratrol-piperazine-curcumin co-crystal.
Figure 11:
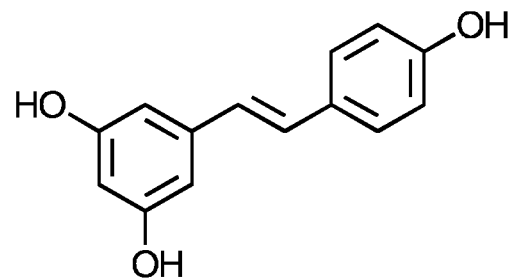
FIG. 11. Chemical structures for resveratrol, piperazine and curcumin (enol and keto form).
Figure 11:
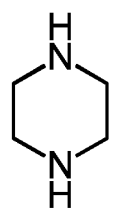
Figure 11:
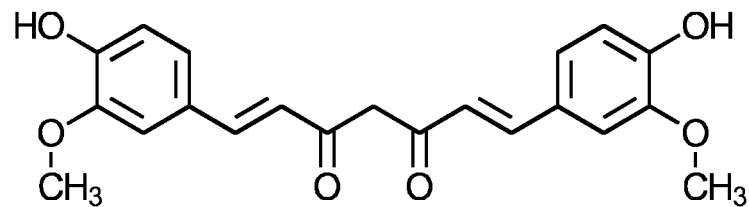
Figure 11:
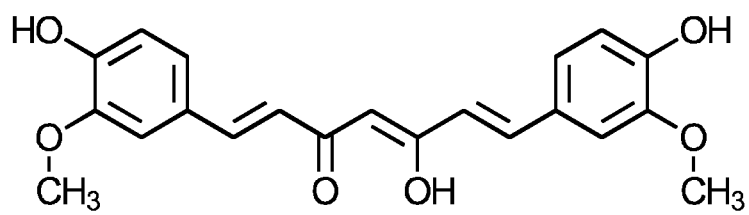

FIG. 9 shows the X-ray powder diffraction pattern of the resveratrol-piperazine-curcumin co-crystal. FIG. 10 shows the DSC thermogram of the resveratrol-piperazine-curcumin co-crystal.

TABLE 5

X-ray powder reflections (up to 33° 2θ) and intensities (normalized) of the resveratrol-piperazine-curcumin co-crystal. The value 2θ [°] represents the diffraction angle in degrees and the value d [Å] represents the specified distances in Å between the lattice planes.

| 2θ [°] | d [Å] | I/I$_o$ [%] |
| --- | --- | --- |
| 4.26 | 20.75 | 28 |
| 11.86 | 7.45 | 45 |
| 12.64 | 7.00 | 48 |
| 13.28 | 6.66 | 39 |
| 15.66 | 5.65 | 53 |
| 16.08 | 5.51 | 60 |
| 16.78 | 5.28 | 98 |
| 17.66 | 5.02 | 59 |
| 20.44 | 4.34 | 61 |
| 23.46 | 3.79 | 78 |
| 23.78 | 3.74 | 61 |
| 24.97 | 3.56 | 58 |
| 25.68 | 3.47 | 100 |

Particularly characteristic peaks in the X-ray powder diffractogram were found to be: d=20.75±0.05 Å, d=7.45±0.05 Å, d=5.28±0.05 Å, d=3.79±0.05 Å, d=3.47±0.05 Å.

The resveratrol-piperazine-curcumin co-crystal was found to be characterized by a fusion temperature of T$_{fus}$=105° C.±5° C., which occurred during thermal analysis using DSC.

The DSC analysis in FIG. 10 indicated a single form of this 3-component co-crystal. All the other experiments involving the three molecules: resveratrol+piperazine+curcumin resulted in mixtures of forms.

It is to be understood that the methods for producing the co-crystals described in the present document can be scaled up or down as long as the ratio of resveratrol, curcumin and piperazine is kept in a starting molar ratio of about 1:1 for the resveratrol-piperazine and curcumin piperazine co-crystals, respectively, or 1:1:1 for the resveratrol-piperazine-curcumin co-crystal.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

Unless expressly described to the contrary, each of the preferred features described herein can be used in combination with any and all of the other herein described preferred features.

The invention claimed is:

1. A method for producing a resveratrol-piperazine co-crystal, Form 1, characterized by having an XRPD pattern comprising peaks at 4.48, 13.32, 16.96, 18.88, 19.16, and 22.84 °2θ±0.2 °2θ, or Form 2, characterized by having an XRPD pattern comprising peaks at 5.87, 12.74, 17.43, 17.70, 20.55, and 21.32 °2θ±0.2 °2θ, said method comprising the steps of:
   a) grinding a mixture comprising resveratrol, piperazine and a solvent selected from ethanol or tetrahydrofuran;
   b) allowing the mixture of step a) to dry thereby providing a further mixture comprising Form 1 when the solvent is ethanol in step a) or Form 2 when the solvent is tetrahydrofuran in step a); and
   c) optionally subjecting the further mixture to further grinding.

2. The method according to claim 1, wherein said method consists of steps a), b) and optionally step c).

3. The method according to claim 1, wherein said grinding of the mixture takes place in a ball mill.

4. The method according to claim 1, wherein the solvent is ethanol and the grinding of the mixture takes place in a mixer mill steel container equipped with stainless steel knives in cross position.

5. The method according to claim 2 wherein said grinding of the mixture takes place in a ball mill.

6. The method according to claim 2, wherein the solvent is ethanol and the grinding takes place in a mixer mill steel container equipped with stainless steel knives in cross position.

7. A resveratrol-piperazine co-crystal, Form 2, obtained by the method of claim 1, wherein said resveratrol-piperazine co-crystal Form 2 has a fusion temperature Tfus of 199° C.±5° C.

8. The method according to claim 1, wherein the method produces Form 1.

9. The method according to claim 1, wherein the method produces Form 2.

10. The method according to claim 1, wherein the method comprises grinding the further mixture.

11. The method according to claim 8, wherein the method comprises grinding the further mixture comprising Form 1.

12. The method according to claim 9, wherein the method comprises grinding the further mixture comprising Form 2.

13. The method according to claim 1, wherein the solvent is tetrahydrofuran and the grinding of the mixture takes place in a mixer mill steel container equipped with stainless steel knives in cross position.

14. The method according to claim 2, wherein the solvent is tetrahydrofuran and the grinding of the mixture takes place in a mixer mill steel container equipped with stainless steel knives in cross position.

* * * * *